US012569170B2

(12) United States Patent
Khan et al.

(10) Patent No.: US 12,569,170 B2
(45) Date of Patent: Mar. 10, 2026

(54) PARAMAGNETIC SODIUM NMR MACROCYCLIC-BASED BIOSENSORS, AND ASSOCIATED METHODS

(71) Applicant: Yale University, New Haven, CT (US)

(72) Inventors: Muhammad Khan, New Haven, CT (US); Sandeep Kumar Mishra, New Haven, CT (US); ABM Zakaria, New Haven, CT (US); Jelena Mihailović, New Haven, CT (US); Daniel Coman, New Haven, CT (US); Fahmeed Hyder, New Haven, CT (US)

(73) Assignee: Yale University, New Haven, CT (US)

( * ) Notice: Subject to any disclaimer, the term of this patent is extended or adjusted under 35 U.S.C. 154(b) by 763 days.

(21) Appl. No.: 17/806,288

(22) Filed: Jun. 10, 2022

(65) Prior Publication Data

US 2022/0400987 A1 Dec. 22, 2022

Related U.S. Application Data

(60) Provisional application No. 63/209,266, filed on Jun. 10, 2021.

(51) Int. Cl.
    *A61B 5/145* (2006.01)
    *A61B 5/055* (2006.01)
    (Continued)

(52) U.S. Cl.
    CPC .......... *A61B 5/14546* (2013.01); *A61B 5/055* (2013.01); *G01R 33/46* (2013.01); *G01R 33/485* (2013.01); *G01R 33/5601* (2013.01)

(58) Field of Classification Search
    CPC .... A61B 5/14546; A61B 5/055; G01R 33/46; G01R 33/441; G01R 33/483; G01R 33/485; G01R 33/5601
    See application file for complete search history.

(56) References Cited

U.S. PATENT DOCUMENTS 4,915,933 A * 4/1990 Matwiyoff ............. A61K 49/06
                                                    424/9.34
6,681,132 B1 * 1/2004 Katz ................. G01R 33/5607
                                                    436/63

(Continued)

OTHER PUBLICATIONS

Winter, Patrick M., and Navin Bansal. "TmDOTP5-as a 23Na shift reagent for the subcutaneously implanted 9L gliosarcoma in rats." Magnetic Resonance in Medicine: An Official Journal of the International Society for Magnetic Resonance in Medicine 45.3 (2001): 436-442. (Year: 2001).*

(Continued)

*Primary Examiner* — Sean D Mattson

(74) *Attorney, Agent, or Firm* — Saul Ewing, LLP; Domingos J. Silva; Kathryn Doyle

(57) ABSTRACT

Paramagnetic sodium NMR biosensors and associated methods are described herein. In one embodiment, a method for detecting sodium ion irregularities in a patient can include administering a volume of metallic biosensors to a region of the patient; and detecting a volume of compartmentalized sodium ions within the region based on the administered volume of metallic biosensors, which comprises a paramagnetic cation (such as, but not limited to, a lanthanide (III) metal ion and/or a transition (II) metal ion) as the core bound to an anionic macrocyclic chelate. In some cases, the volume of compartmentalized sodium ions can further include a volume of intracellular sodium ions, a volume of interstitial sodium ions, a volume of blood sodium ions, or a combination thereof.

15 Claims, 16 Drawing Sheets

(51) Int. Cl.
    *G01R 33/46*          (2006.01)
    *G01R 33/485*       (2006.01)
    *G01R 33/56*          (2006.01)

(56)                    References Cited

U.S. PATENT DOCUMENTS

| | | | |
|---|---|---|---|
| 8,880,146 B1 * | 11/2014 | Schepkin | A61B 5/055 |
| | | | 382/131 |
| 2004/0258618 A1 * | 12/2004 | Terreno | C07D 257/02 |
| | | | 424/9.3 |
| 2022/0033426 A1 | 2/2022 | Zakaria et al. | |

OTHER PUBLICATIONS

Tsitovich, Pavel B., and Janet R. Morrow. "Macrocyclic ligands for Fe (II) paraCEST and chemical shift MRI contrast agents." Inorganica Chimica Acta 393 (2012): 3-11. (Year: 2012).*

Madelin, Guillaume, et al. "A method for estimating intracellular sodium concentration and extracellular volume fraction in brain in vivo using sodium magnetic resonance imaging." Scientific reports 4.1 (2014): 4763. (Year: 2014).*

Schepkin, Victor D., et al. "Sodium and proton diffusion MRI as biomarkers for early therapeutic response in subcutaneous tumors." Magnetic resonance imaging 24.3 (2006): 273-278. (Year: 2006).*

Bansal, Navin, et al. "In vivo Na-23 MR imaging and spectroscopy of rat brain during TmDOTP5-infusion." Journal of Magnetic Resonance Imaging 2.4 (1992): 385-391. (Year: 1992).*

Khan, Muhammad H., et al. "Imaging the transmembrane and transendothelial sodium gradients in gliomas." Scientific Reports 11.1 (2021): 6710. (Year: 2021).*

* cited by examiner

Inner

Outer

Outer: +TmDOTP$^{5-}$          Inner: No TmDOTP$^{5-}$

Inner: +TmDOTP$^{5-}$          Outer: No TmDOTP$^{5-}$

FIG. 2B    Inside Tumor (*In vivo*)

FIG. 2C    Outside Tumor (*In vivo*)

FIG. 2D    Blood Sample (*In vitro*)

Before TmDOTP⁵⁻          After TmDOTP⁵⁻

Sorafenib

TmDOTP⁵⁻

FIG. 10C    $\Gamma_0$

FIG. 10D    $\Gamma_{Tm}$

FIG. 10E    $\Delta Na^+_{cmd}$

FIG. 10F    $\Delta Na^+_{mem}$

FIG. 13B $^{23}$Na Chemical Shift Induced by 2 mM TmDOTP$^{5-}$ in the Presence of Competing Cations
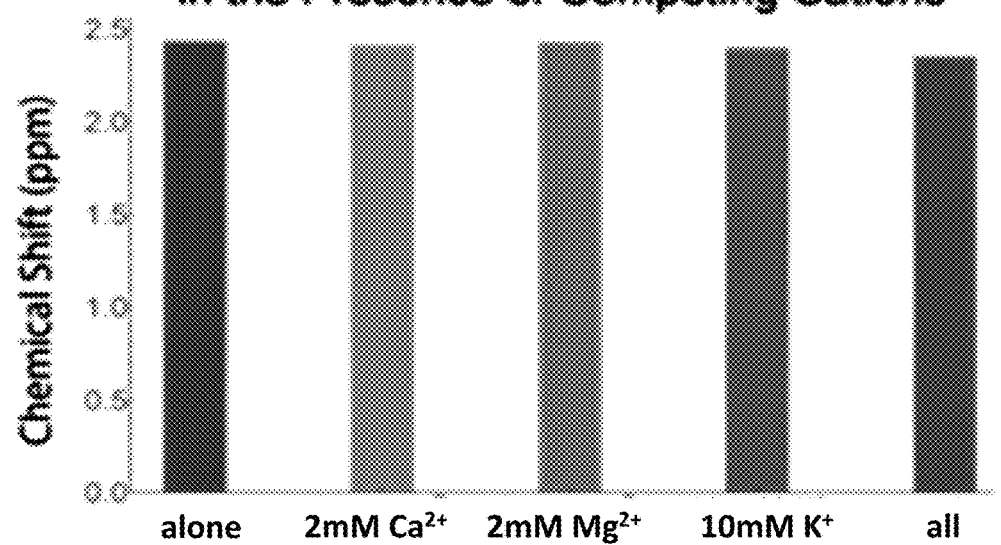
FIG. 13C $^{23}$Na Line Width Induced by 2 mM TmDOTP$^{5-}$ in the Presence of Competing Cations
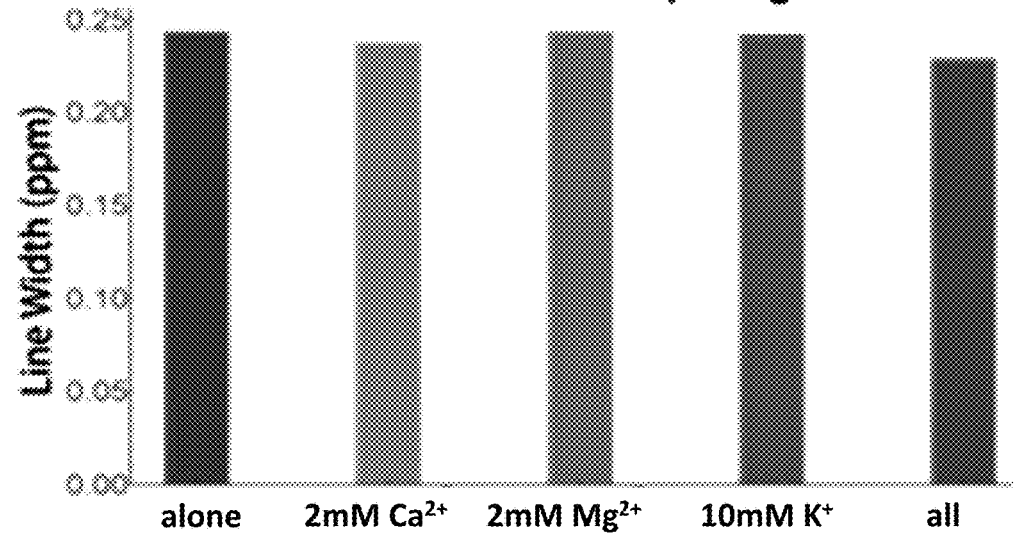

PARAMAGNETIC SODIUM NMR MACROCYCLIC-BASED BIOSENSORS, AND ASSOCIATED METHODS

CROSS-REFERENCE TO RELATED APPLICATIONS

The present application claims priority under 35 U.S.C. § 119(e) to U.S. Provisional Application No. 63/209,266 filed Jun. 10, 2021, which is hereby incorporated herein by reference in its entirety.

STATEMENT REGARDING FEDERALLY SPONSORED RESEARCH OR DEVELOPMENT

This invention was made with government support under EB-023366 and MH-067528 awarded by National Institutes of Health. The government has certain rights in the invention.

BACKGROUND OF THE INVENTION

Sodium ($Na^+$) concentration is normally low intracellularly (~10 mM) and high in blood and interstitial spaces (~150 mM), producing a strong transmembrane $Na^+$ gradient ($\Delta Na^+_{mem}$~140 mM) and a weak transendothelial $Na^+$ gradient ($\Delta Na^+_{end}$~0 mM). The $\Delta Na^+_{mem}$ is coupled to the cell membrane potential ($V_m$) which is relevant for nerve signaling, muscle activity, and osmoregulation, while the $\Delta Na^+_{end}$ impacts bicarbonate and proton ($H^+$) ion transport between interstitial and blood compartments to signify blood-brain barrier (BBB) integrity.

The sodium-potassium pump transports $Na^+$ against its electrochemical gradient by consuming adenosine triphosphate (ATP) generated through oxidative phosphorylation. In cancer, glycolysis is upregulated in relation to oxidative phosphorylation even with sufficient oxygen. Aerobic glycolysis generates excessive amounts of $H^+$ and lactate, which are extruded into the interstitial milieu, lowering the pH of the tumor microenvironment. Since both the cell membrane and BBB regulate the ionic composition of the interstitial fluid, in certain embodiments maintaining $\Delta Na^+_{mem}$ and $\Delta Na^+_{end}$ becomes unsustainable in the tumor neurovascular unit. Activity of voltage-gated $Na^+$ channels on the cancer cell membrane helps regulate proliferation, migration, and invasion rather than excitability. Similar to pH dysregulation in cancer, electrolyte imbalance also has a role in tumorigenesis. Thus, being able to measure $[Na^+]$ across different compartments in vivo could be considered as an important biomarker of cancer.

Hyperpolarized $V_m$ corresponds to quiescent cell cycle stages ($G_0$ phase), and depolarized $V_m$ is needed for proliferative/replicative stages (M phase). Therefore, $\Delta Na^+_{mem}$ is a biomarker for tumorigenicity and tumor aggressiveness. Determining $[Na^+]$ in the interstitial milieu usually involves inserting microelectrodes through the skull and reading voltage differences across cellular compartments. In addition to issues of accurate microelectrode positioning and tissue penetration, such invasive techniques are challenging for human translation.

Angiogenesis is a crucial part of tumor growth. Unlike normal tissues, the immature tumor vasculature exhibits saccular formations, hyperbranching, and twisted patterns that cause the BBB to become leaky. Prior cancer research could not measure $[Na^+]$ in blood presumably due to micro-hemorrhage concerns from ruptured blood vessels with microelectrodes. But given the gamut of anti-angiogenic therapies for GBM, it is desirable to measure $\Delta Na^+_{end}$ non-invasively.

Nuclear magnetic resonance (NMR) can detect the isotope sodium-23 ($^{23}Na$), a spin-3/2 quadrupolar nucleus. $^{23}Na$ is 100% abundant and provides the second-strongest endogenous NMR signal in vivo, next to hydrogen (H) which is a spin-1/2 nucleus. $^{23}Na$ magnetic resonance imaging (MRI) has greatly impacted stroke and ischemia research, but reflects total sodium ($Na^+_T$) because $^{23}Na$-MRI signals from blood ($Na^+_b$), interstitial ($Na^+_o$), and intracellular ($Na^+_i$) compartments are difficult to separate. $^{23}Na$-MRI methods are based on apparent diffusion coefficient (ADC), inversion recovery, and multiple quantum filtering (MQF) attempt to separate free (i.e., so called "unbound" or aqueous) and so called "bound" $Na^+$ signals. Due to the volumes of these sub-populations of $Na^+$, these approaches suffer from low sensitivity and specificity. Moreover, diffusion methods necessitate large magnetic field gradients due to low gyromagnetic ratio ($\gamma_{Na}$) and short longitudinal/transverse relaxation times ($T_1$, $T_2$) for $^{23}Na$. These $^{23}Na$-MRI methods are somewhat limited for probing the aqueous $Na^+_i$ signal because they cannot fully suppress major contributions from aqueous $Na^+_b$ and $Na^+_e$, both of which dominate the $Na^+_T$ signal. Thus, quantification of transmembrane ($\Delta Na^+_{mem} = Na^+_e - Na^+_i$) and transendothelial ($\Delta Na^+_{end} = Na^+_b - Na^+_e$) gradients has been challenging with $^{23}Na$-MRI. While detecting $Na^+_T$ is useful clinically, $\Delta Na^+_{end}$ and $\Delta Na^+_{mem}$ may help reveal relevant information about BBB viability and cellular proliferative/oncogenic potential in solid tumors.

Another approach to separate aqueous $Na^+$ signals in vivo involves intravenous administration of an exogenous paramagnetic but polyanionic contrast agent ($paraCA^{n-}$). The $paraCA^{n-}$ comprises a lanthanide (III) metal ion (or a transition (II) metal ion) as the core bound to an anionic macrocyclic chelate. Since the $paraCA^{n-}$ extravasates into interstitial space of most organs but does not enter cells, only $Na^+_e$ and $Na^+_b$ are attracted to the $paraCA^{n-}$ and experience a shift in the $^{23}Na$ resonance frequency (depending on degree of $paraCA^{n-}$ extravasation in each compartment) to separate the $^{23}Na$ magnetic resonance spectroscopic imaging (MRSI) signals between $Na^+_b$, $Na^+_e$ and $Na^+_i$. While these paramagnetic effects will also shorten $^{23}Na$ relaxation times slightly, the peak's integral remains unaffected if data are acquired under fully relaxed conditions, and the peak's shift can still be precise when there is marginal line broadening although integral bands will need to be widened so as to accurately estimate concentration. Proof-of-concept for this has been demonstrated in situ for the heart and liver. Given the compromised BBB in tumors relative to healthy tissue, the $^{23}Na$-MRSI technique in conjunction with $paraCA^{n-}$ is particularly efficacious in studying brain tumors.

The most effective $paraCA^{n-}$ for aqueous compartmental $^{23}Na$ separation is the thulium(III) cation ($Tm^{3+}$) complexed with 1,4,7,10-tetraazacyclododecane-1,4,7,10-tetrakis (methylenephosphonate) ($DOTP^{8-}$) to form $TmDOTP^{5-}$ (FIG. 1A). $TmDOTP^{5-}$ has many applications in animal models, both with $^1H$-NMR and $^{23}Na$-NMR, demonstrating that these $Tm^{3+}$ agents are non-toxic at the doses presently being used for preclinical studies. Particularly, $TmDOTP^{5-}$ has been infused intravenously to induce $^{23}Na$ compartmental signal separation in healthy and tumor-bearing rats. However, these studies only detected non-localized $^{23}Na$ signals, and thus could not differentiate between $Na^+$ across tissues.

BRIEF SUMMARY OF THE DISCLOSURE

The present disclosure provides a method for detecting sodium ion irregularities in a patient. In certain embodiments, the method comprises administering a volume of metallic biosensors, which comprises a paramagnetic cation as the core bound to an anionic macrocyclic chelate. In certain embodiments, the method comprises detecting a volume of compartmentalized sodium ions within the region based on the administered volume of metallic biosensors. In certain embodiments, the administering is systemically to the patient and/or to specific region of the patient's body. In certain embodiments, the paramagnetic cation comprises a lanthanide (III) metal ion and/or a transition (II) metal ion.

BRIEF DESCRIPTION OF THE DRAWINGS

For a fuller understanding of the nature and desired objects of the present invention, reference is made to the following detailed description taken in conjunction with the accompanying drawing figures wherein like reference characters denote corresponding parts throughout the several views.

FIGS. 1A-1G depicts shifting mechanism of the $^{23}$Na resonance in vitro. FIG. 1A depicts chemical structure of sodium thulium (III) 1,4,7,10-tetraazacyclododecane-1,4,7,10-tetrakis(methylenephosphonate) (Na$_5$TmDOTP). The TmDOTP$^{5-}$ complex consists of the Tm$^{3+}$ ion chelated with DOTP$^{8-}$. Each phosphonate-containing pendant arm on TmDOTP$^{5-}$ has electron-donating groups on the oxygen atoms to stabilize the Tm$^{3+}$ conjugation with DOTP$^{8-}$. The −5 charge cooperatively attracts five Na$^+$ ions, which experience a shift in the observed $^{23}$Na resonance that is dependent on [TmDOTP$^{5-}$]. FIG. 1B depicts in vivo, prior to TmDOTP$^{5-}$ administration (left), the $^{23}$Na spectrum yields only a single peak representing the total sodium (Na$^+_T$) comprising blood (Na$^+_b$), interstitial (Na$^+_e$), and intracellular (Na$^+_i$) compartments. Following TmDOTP$^{5-}$ administration (right), the peaks become spectroscopically separable based on [TmDOTP$^{5-}$] in each compartment. Integrals of these peaks will be representative of aqueous [Na$^+$] in each compartment. FIG. 1C depicts a two-compartment coaxial cylinder tube setup that was employed for in vitro observation of the chemical shift separation scheme. The inner tube (smaller volume) was filled with 150 mM NaCl, while the outer tube (larger volume) was filled with the same solution in addition to various amounts of TmDOTP$^{5-}$, each subject to different pH conditions. Thus, all $^{23}$Na spectra from this phantom setup displayed a small unshifted peak from the inner compartment and a larger shifted peak. The outer-to-inner volume ratio was 8.6, explaining the difference in sizes of the peaks. Exemplary traces of $^{23}$Na spectra show that the shift is much more sensitive to [TmDOTP$^{5-}$] (2.77 ppm/mM) than to variations in pH (0.25 ppm/pH unit) or temperature (0.03 ppm/° C.). The downfield peaks in the red, blue, and/or black spectra are shifted differently due to varying TmDOTP$^{5-}$ concentrations, and these shifts exceed those caused by pH, but all these shifts are detectable independent of broadening caused by TmDOTP$^{5-}$. FIGS. 1D-1E show that temperature, pH, and [TmDOTP$^{5-}$] all contribute to variations of the $^{23}$Na chemical shift. However, these plots depict ranges of pH and temperature that are unlikely for in vivo settings (i.e., changes over 2 full pH units and temperature changes over 15° C.). Moreover, [Na$^+$] in vivo (~150 mM in blood and interstitial space) is extremely high compared to [TmDOTP$^{5-}$]. Therefore, variations in $^{23}$Na chemical shift are primarily dependent on

[TmDOTP$^{5-}$]/[Na$^+$] thereby rendering plots (FIG. 1F) pH and (FIG. 1G) temperature dependencies negligible. Data points were fit to Chebyshev rational polynomials using TableCurve 3D v4.0.05.

Figure 2A:
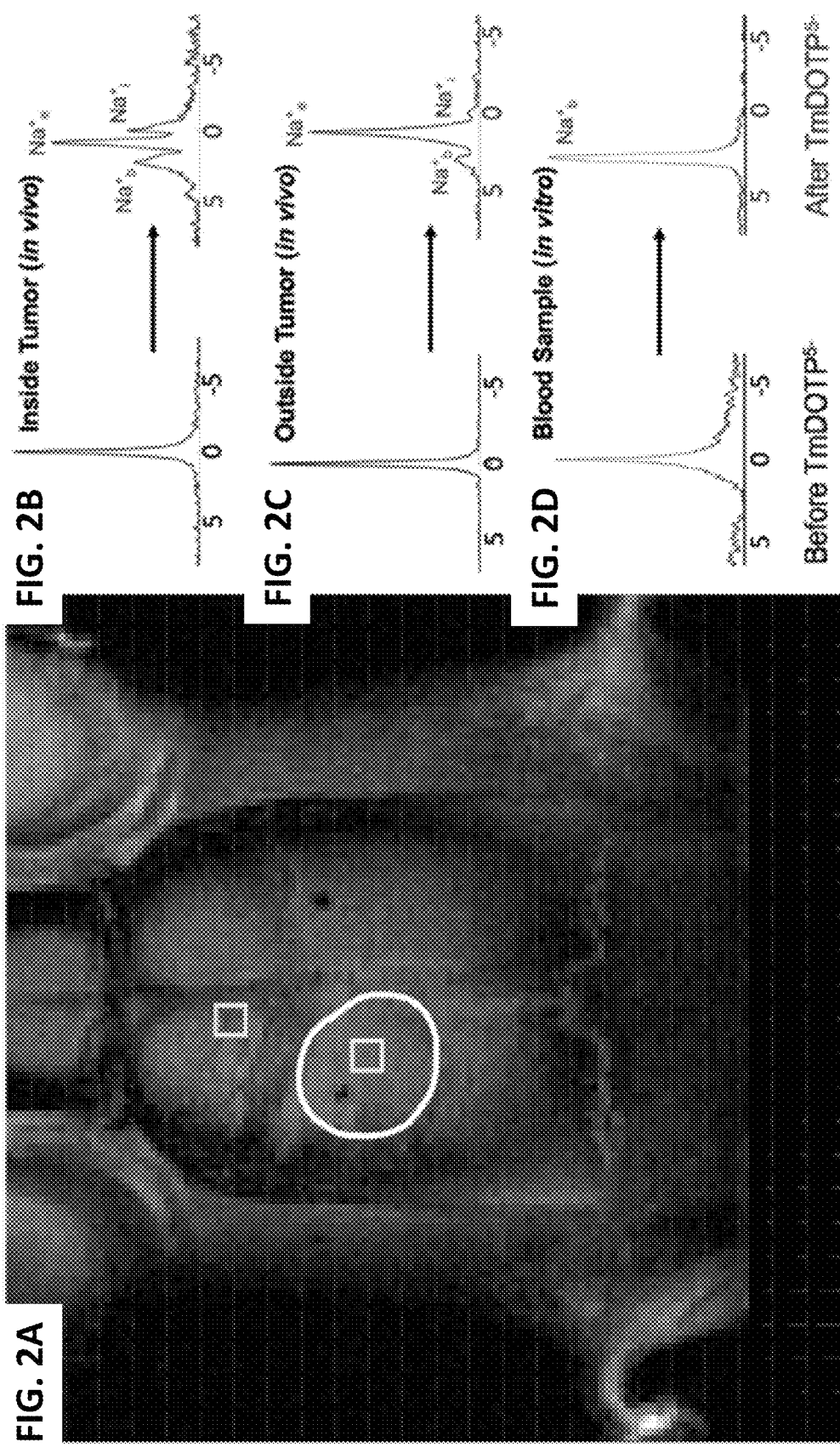

FIGS. 2A-2D depicts a demonstration of $^{23}$Na peak separation in vivo following TmDOTP$^{5-}$ administration into a rat bearing a U251 tumor in the brain. FIG. 2A depicts $^1$H-MRI of an axial slice displaying the anatomical tumor boundary (outline). The $^{23}$Na-MRSI is overlaid on top of the $^1$H-MRI. Candidate voxels, FIG. 2B inside the tumor and FIG. 2C outside the tumor, are indicated (boxes). Before TmDOTP$^{5-}$ delivery, a single $^{23}$Na peak was observed at 0 ppm, corresponding to total sodium (Na$^+_T$), both inside and outside the tumor (black spectra). Following TmDOTP$^{5-}$ delivery, compartmental peak separation was achieved to varying extents throughout the brain (blue spectra). In FIG. 2B, within the tumor, this separation was most pronounced due to a compromised blood-brain barrier (BBB), which permits substantial accumulation of TmDOTP$^{5-}$ in the interstitial space. In FIG. 2C, outside of the tumor, such a high degree of extravasation would not be possible, but some shifting is still observed. The TmDOTP$^{5-}$ distribution in the brain warrants labeling the most shifted peak as blood sodium (Na$^+_b$), which occurred consistently around 2 ppm. The unshifted peak, which has no access to TmDOTP$^{5-}$, is intracellular sodium (Na$^+_i$). The intermediate peak, therefore, is interstitial sodium (Na$^+_e$), which is shifted more inside the tumor than outside in healthy tissue. Similar spectroscopic patterns are observed throughout all voxels in vivo. In FIG. 2D, in vitro analysis of blood samples from the tumor-bearing rat show that the $^{23}$Na blood peak occurred around 2 ppm, which coincided with the most-shifted peak observed in tumor voxels. This confirmed that the most-shifted peak in the observed $^{23}$Na spectra after TmDOTP$^{5-}$ comes from blood. All spectra were magnitude-corrected and line-broadened by 10 Hz.

Figures 3A, 3B:
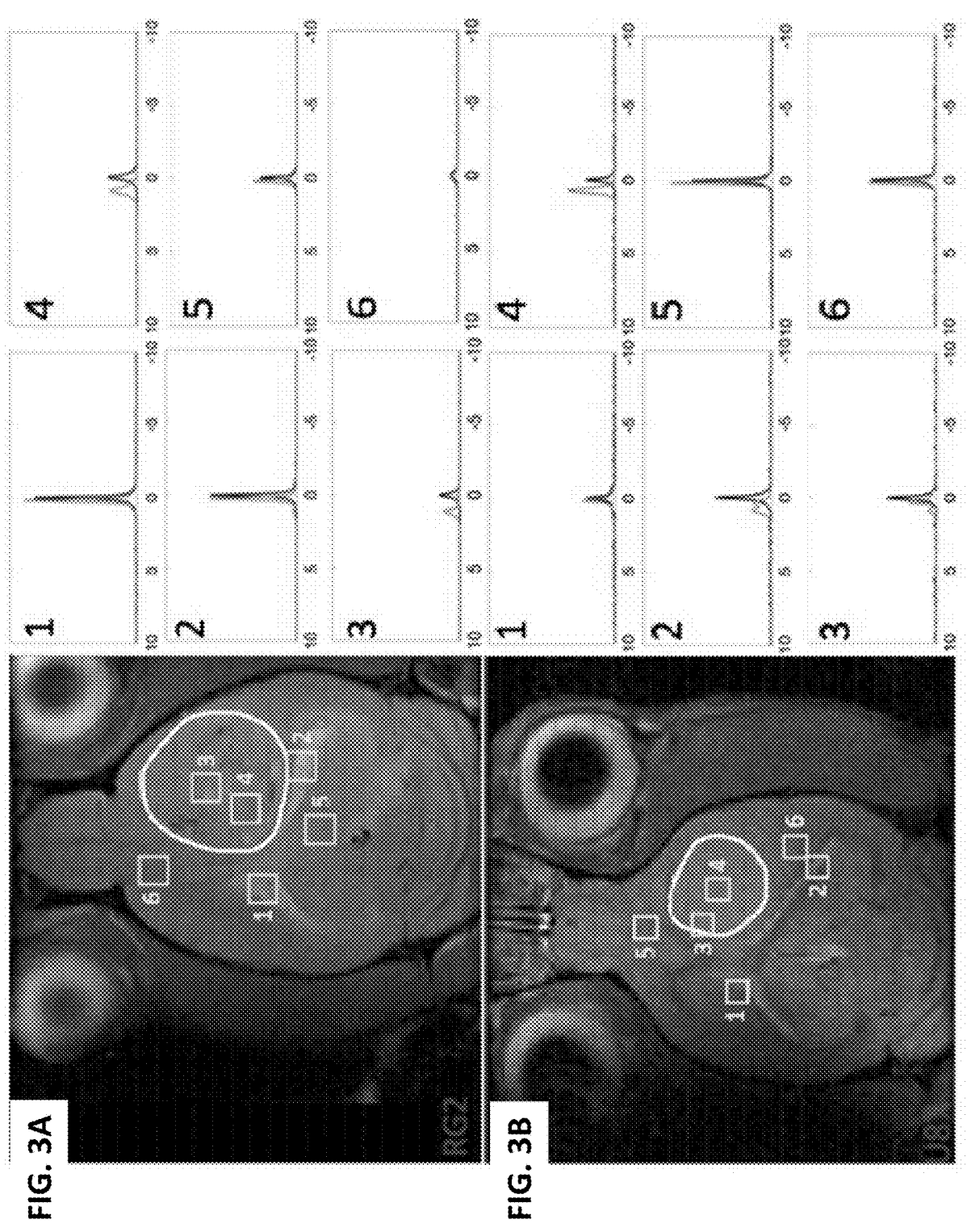

FIGS. 3A-3B depict a comparison of $^{23}$Na peak separation in rats bearing RG2 and U87 tumors. For rats bearing an RG2 (FIG. 3A) and U87 tumor (FIG. 3B), the tumor boundary is outlined, with voxels of interest indicated in squares (with numbers), and spectra acquired before and after TmDOTP$^{5-}$ delivery shown in black and green, respectively. Tumor voxels (3) and (4) in FIG. 3A RG2 and FIG. 3B U87 tumor rats exhibited a fair amount of peak separation due to the leaky BBB. Na$^+_b$ shift was consistently around 2 ppm, and Na$^+_i$ shift was at 0 ppm, whereas Na$^+_e$ shift in the tumor was in the range 0.5-1 ppm. Healthy tissue voxels (5) and (6) in FIG. 3A RG2 and FIG. 3B U87 tumor rats were slightly shifted in the downfield direction, suggesting the paramagnetic effects of TmDOTP$^{5-}$ reach the interstitial space even with limited extravasation. Ventricular voxels (1) and (2) in FIG. 3A RG2 and FIG. 3B U87 tumor rats displayed a single unshifted Lorentzian peak before and a shifted Lorentzian peak after TmDOTP$^{5-}$ injection. This is attributed to the dominant $^{23}$Na signal contribution in the ventricles coming from cerebrospinal fluid (CSF), which contains free (i.e., unbound) aqueous Na$^+$. The position of the shifted ventricle peak coincided with the Na$^+_e$ peak position in other regions of the brain. This agrees with expectation because CSF is in physical contact with the interstitial space with free exchange of aqueous Na$^+$ between the two compartments. Similar spectroscopic patterns are observed throughout all voxels in vivo. All spectra were magnitude-corrected and line-broadened by 10 Hz.

Figure 4:
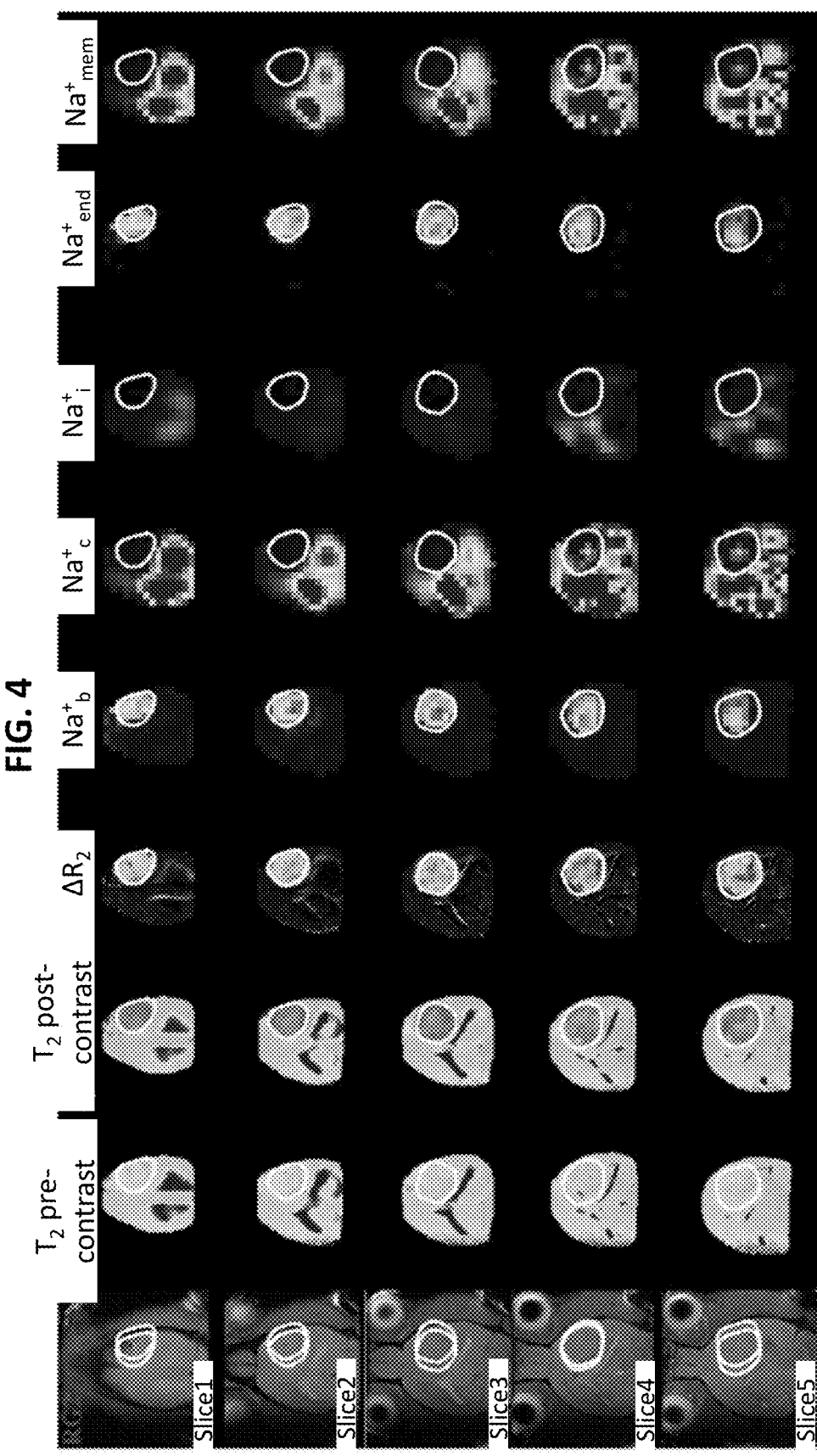

FIG. 4 depicts spatial distributions of compartmentalized $^{23}$Na signals (Na$^+_b$, Na$^+_e$, Na$^+_i$) as well as transendothelial (ΔNa$^+_{end}$) and transmembrane (ΔNa$^+_{mem}$) gradients in an RG2 tumor. The high-resolution $^1$H-MRI data are shown in the left four columns, whereas the lower resolution $^{23}$Na-MRSI data are shown in the next five columns on the right. The left column shows the tumor location (outline) on the anatomical $^1$H-MRI (left), whereas the next two columns show the $T_2$ maps (range shown: 0-100 ms) before and after TmDOTP$^{5-}$ injection, and the subsequent column depicts the $\Delta R_2$ map (i.e., difference between $1/T_2$ maps before and after, range shown: 0-30 s$^{-1}$), which is proportional to [TmDOTP$^{5-}$] in healthy and tumor tissues. Since $\Delta R_2$ values are more heterogeneous within the tumor, the $^{23}$Na-MRSI data are needed to separate the blood and interstitial compartment signals for the tumor. Since the integral of each $^{23}$Na peak represents the [Na$^+$], the respective three columns show the integral maps of Na$^+_b$, Na$^+_e$, and Na$^+_i$ from left to right (i.e., $\int$Na$^+_b$, $\int$Na$^+_e$, $\int$Na$^+_i$). The last two columns on the right show $\Delta$Na$^+_{end}$=$\int$Na$^+_b$-$\int$Na$^+_e$ and $\Delta$Na$^+_{mem}$=$\int$Na$^+_e$-$\int$Na$^+_i$. The $\int$Na$^+_b$ map reveals low values in healthy tissue compared to tumor tissue, and within the tumor boundary a high degree of heterogeneity. The $\int$Na$^+_e$ map reveals low values in tumor and normal tissues, but within the tumor boundary a small degree of heterogeneity is visible while ventricular voxels show very high values. The $\int$Na$^+_i$ map reveals low values ubiquitously except some ventricular voxels. The $\Delta$Na$^+_{end}$ map reveals dramatically high values within the tumor only. The $\Delta$Na$^+_{end}$ was driven primarily by an increase of $\int$Na$^+_b$ inside the tumor and which was more pronounced in superficial regions of the brain compared to deeper slices. The $\Delta$Na$^+_{mem}$ map shows low values in tumor tissue compared to normal tissue, although ventricular voxels show very high values. The $\Delta$Na$^+_{mem}$ is driven primarily by decreased $\int$Na$^+_e$ and thus shows similar level of heterogeneity as the $\int$Na$^+_e$ map. All maps use the same color scale and are relative.

Figures 5A, 5B, 5C:
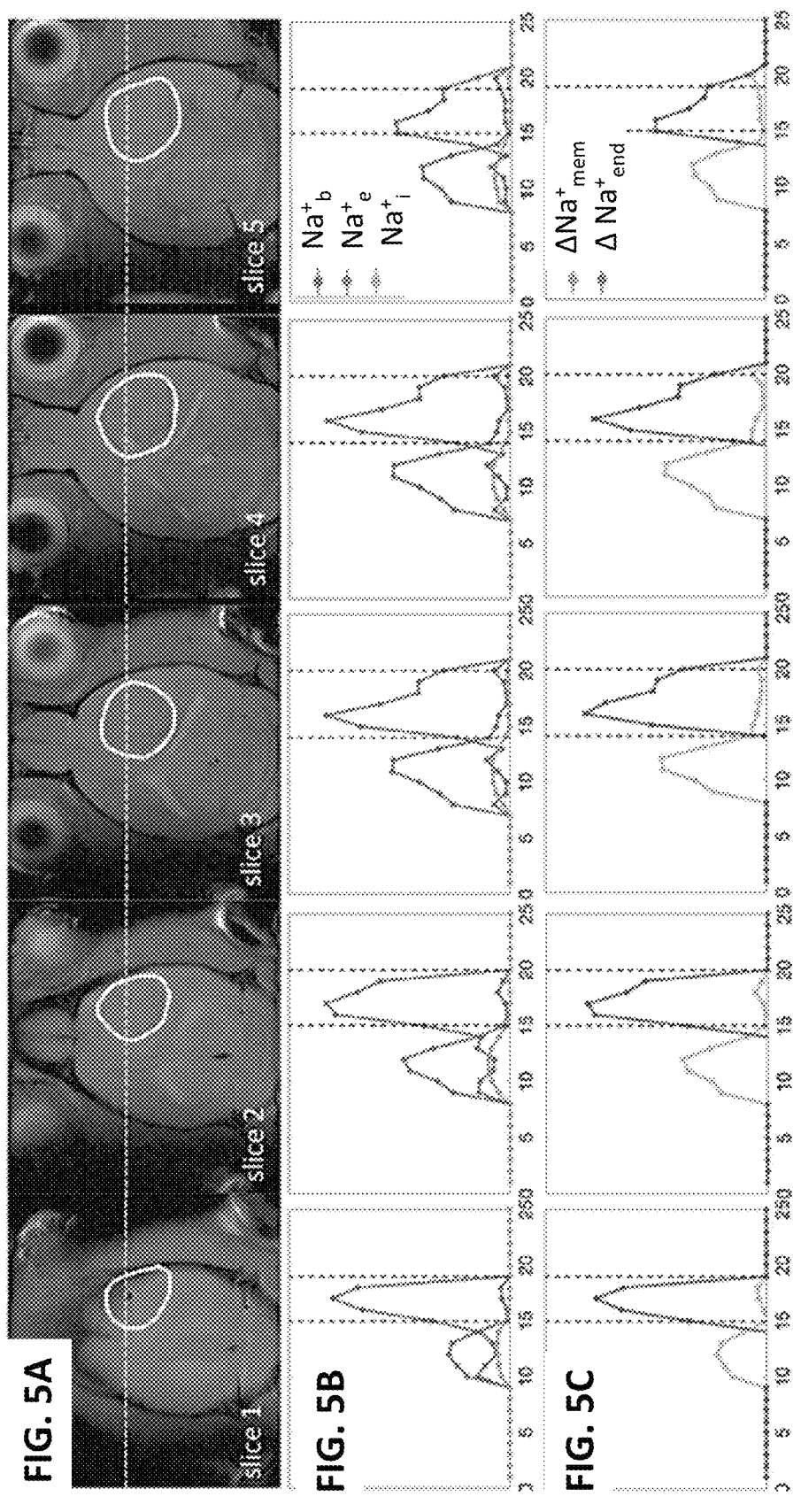

FIGS. 5A-5C depict coronal projections of compartmentalized $^{23}$Na signals (Na$^+_b$, Na$^+_e$, Na$^+_i$) as well as transendothelial ($\Delta$Na$^+_{end}$) and transmembrane ($\Delta$Na$^+_{mem}$) gradients in an RG2 tumor. FIG. 5A depicts axial $^1$H-MRI indicating the tumor (white outline) across slices (same as FIG. 4), where the yellow line indicates the position for a coronal projection. FIG. 5B depicts spatially varying $^{23}$Na signals for Na$^+_b$, Na$^+_e$, and Na$^+_i$ that are shown with different lines, where the vertical black lines indicate the tumor boundary. The Na$^+_b$ signal is clearly elevated in the tumor, and most elevated in slices 1-4 (or superficially). Behavior of Na$^+_b$ signal is inversely related to Na$^+_e$ signal, which is high outside the tumor and weaker inside the tumor. While intratumoral Na$^+_b$ signal is high in slices 1-4, the peritumoral Na$^+_e$ signal is highest in slices 3-4. Comparatively, the Na$^+_i$ signal does not vary significantly across slices, but slightly lower inside the tumor than outside the tumor. FIG. 5C depicts behaviors of $\Delta$Na$^+_{mem}$ and $\Delta$Na$^+_{end}$ signals closely mimic patterns of Na$^+_e$ and Na$^+_b$ signals, respectively, indicating that each of those Na$^+$ compartments is the primary driver of the respective Na$^+$ gradient.

Figures 6A, 6B, 6C:
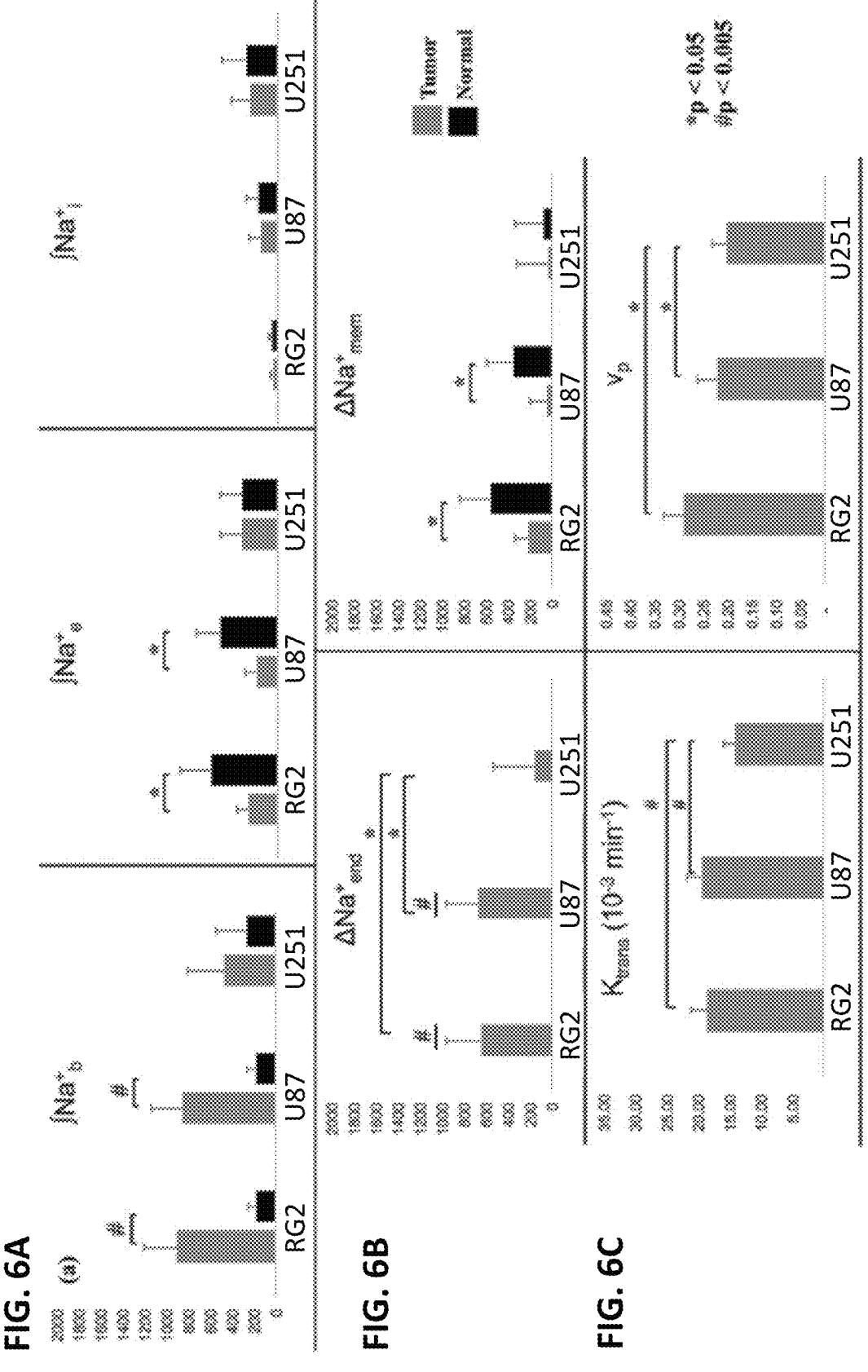

FIGS. 6A-6C depict statistical comparisons between intracellular, interstitial, and vascular compartments across RG2, U87, and U251 tumors with $^{23}$Na-MRSI and $^1$H-DCE-MRI, where the latter is a reflection vascular properties revealed by extravasation of an injected gadolinium agent. FIG. 6A depicts the relation between $\int$Na$^+_b$, $\int$Na$^+_e$ and $\int$Na$^+_i$ across tumor and healthy tissues. For the RG2 and U87 tumors, the $\int$Na$^+_b$ values were significantly higher than normal tissue (p<0.005, #). Also, for these tumors, the $\int$Na$^+_e$ values were significantly lower than normal tissue (p<0.05, *). The mean values for the U251 tumor roughly followed the same trend but were not significant. Furthermore, there was no significant difference between $\int$Na$^+_i$ values in tumor and normal tissues for any of the three tumor types. FIG. 6B depicts relations between tumor and normal tissues for $\Delta$Na$^+_{end}$ and $\Delta$Na$^+_{mem}$ for the three tumor types. Tumor $\Delta$Na$^+_{end}$ values were significantly larger than normal values (p<0.005, #), which were non-positive (data not shown). Moreover, $\Delta$Na$^+_{end}$ in RG2 and U87 tumors was significantly greater than in the U251 tumor (p<0.05, *), indicative of vascular differences between the tumor types. $\Delta$Na$^+_{mem}$ values were, on average, weaker in tumor compared to normal tissue, but significant only in RG2 and U87 tumors (p<0.05, *). Based on FIGS. 5A-5C, it is clear that the relation between $\Delta$Na$^+_{end}$ and $\Delta$Na$^+_{mem}$ is negative. FIG. 6C depicts $^1$H-DCE-MRI data for the volume transfer coefficient (K$^{trans}$) and plasma volume fraction (v$_p$) values, which are known to reveal information regarding vascular structure and function. K$^{trans}$ follows the same patterns as $\int$Na$^+_b$ and $\Delta$Na$^+_{end}$ across tumor types. K$^{trans}$ (p<0.005, #) and v$_p$ (p<0.05, *) were both significantly larger in RG2 and U87 tumors, compared to U251.

Figures 7A, 7B, 7C:
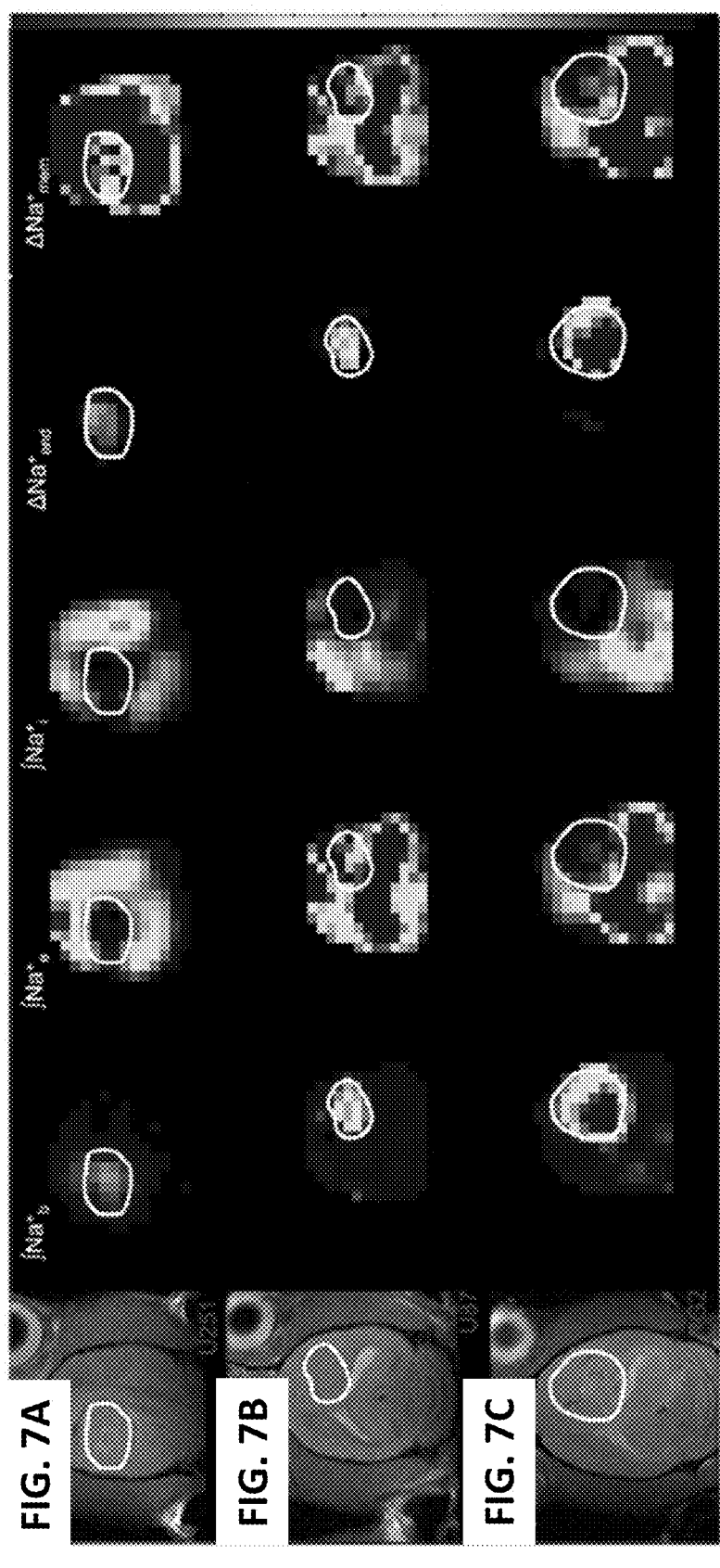

FIGS. 7A-7C depicts representative maps of compartmentalized $^{23}$Na signals (Na$^+_b$, Na$^+_e$, Na$^+_i$) as well as transendothelial ($\Delta$Na$^+_{end}$) and transmembrane ($\Delta$Na$^+_{mem}$) gradients in U251, U87, and RG2 tumors. The left column shows the tumor location (outline) on the anatomical $^1$H-MRI for animals bearing U251 (FIG. 7A), U87 (FIG. 7B), and RG2 (FIG. 7C) tumors. The respective three columns show $\int$Na$^+_b$, $\int$Na$^+_e$, and $\int$Na$^+_i$ maps. The last two columns on the right show the $\Delta$Na$^+_{end}$ and $\Delta$Na$^+_{mem}$ maps. In all tumors the $\int$Na$^+_b$ and $\int$Na$^+_e$ are high and low, respectively, and thus are the main drivers for a high $\Delta$Na$^+_{end}$ and a low $\Delta$Na$^+_{mem}$.

Figure 8:
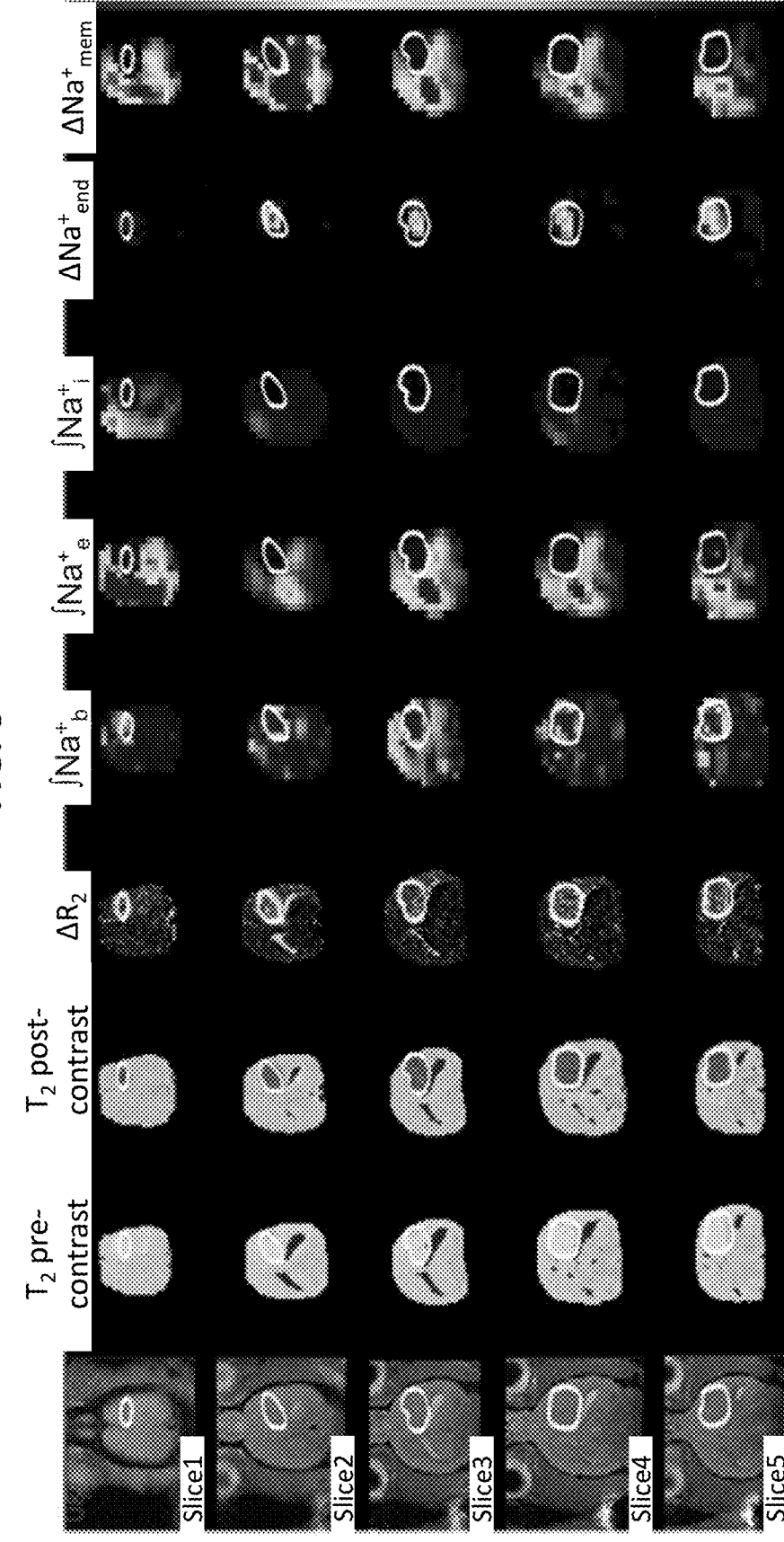

FIG. 8 depicts spatial distributions of compartmentalized $^{23}$Na signals (Na$^+_b$, Na$^+_e$, Na$^+_i$) as well as transendothelial ($\Delta$Na$^+_{end}$) and transmembrane ($\Delta$Na$^+_{mem}$) gradients in a U87 tumor. The high-resolution $^1$H-MRI data are shown in the left four columns, whereas the lower resolution $^{23}$Na-MRSI data are shown in the next five columns on the right. The left column shows the tumor location (outline) on the anatomical $^1$H-MRI (left), whereas the next two columns show the $T_2$ maps (range shown: 0-100 ms) before and after TmDOTP$^{5-}$ injection, and the subsequent column depicts the $\Delta R_2$ map (i.e., difference between $1/T_2$ maps before and after, range shown: 0-30 s$^{-1}$), which is proportional to [TmDOTP$^{5-}$] in healthy and tumor tissues. Since $\Delta R_2$ values are more heterogeneous within the tumor, the $^{23}$Na-MRSI data can be used to separate the blood and interstitial compartment signals for the tumor. Since the integral of each $^{23}$Na peak represents the [Na$^+$], the respective three columns show the integral maps of Na$^+_b$, Na$^+_e$, and Na$^+_i$ from left to right (i.e., $\int$Na$^+_b$, $\int$Na$^+_e$, $\int$Na$^+_i$). The last two columns on the right show $\Delta$Na$^+_{end}$=$\int$Na$^+_b$-$\int$Na$^+_e$ and $\Delta$Na$^+_{mem}$=$\int$Na$^+_e$-$\int$Na$^+_i$. The $\int$Na$^+_b$ map reveals low values in healthy tissue compared to tumor tissue, and within the tumor boundary a high degree of heterogeneity. The $\int$Na$^+_e$ map reveals low values in tumor and normal tissues, but within the tumor boundary a small degree of heterogeneity is visible while ventricular voxels show very high values. The $\int$Na$^+_i$ map reveals low values ubiquitously except some ventricular voxels. The $\Delta$Na$^+_{end}$ map reveals dramatically high values within the tumor. The $\Delta$Na$^+_{end}$ was driven primarily by an increase of $\int$Na$^+_b$ inside the tumor and which was more pronounced in superficial regions of the brain compared to deeper slices. The $\Delta$Na$^+_{mem}$ map shows low values in tumor tissue compared to normal tissue, although ventricular voxels show very high values. The $\Delta$Na$^+_{mem}$ is driven primarily by decreased $\int$Na$^+_e$ and

US 12,569,170 B2

7 thus shows similar level of heterogeneity as the $\int Na^+_e$ map. All maps use the same color scale and are relative.

Figure 9:
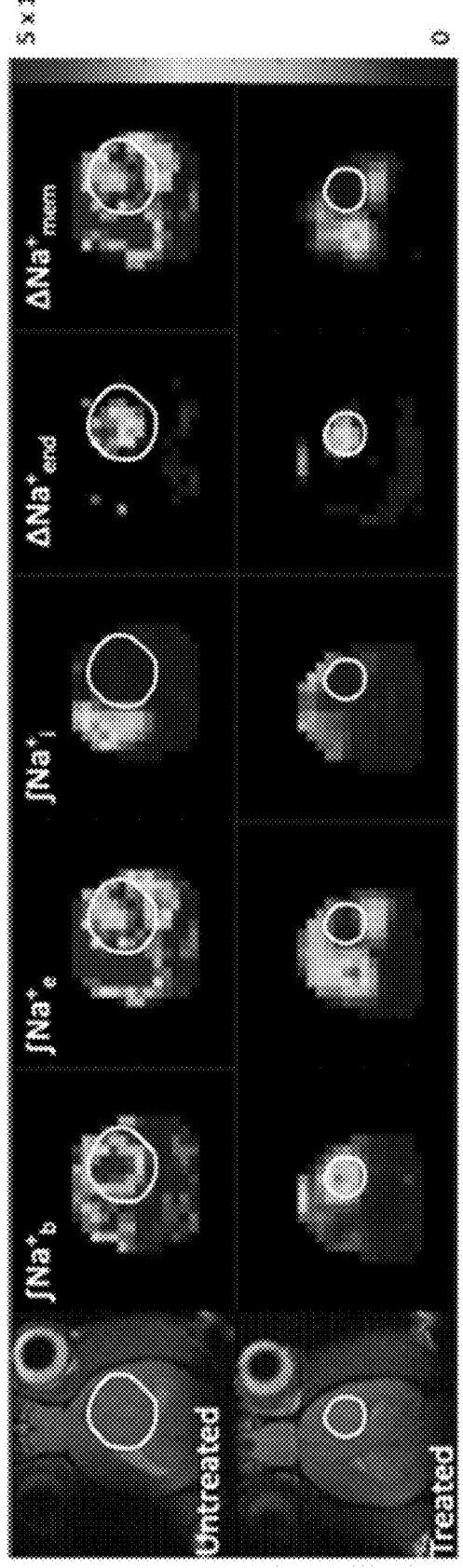
Figures 11A, 11B, 11C, 11D:
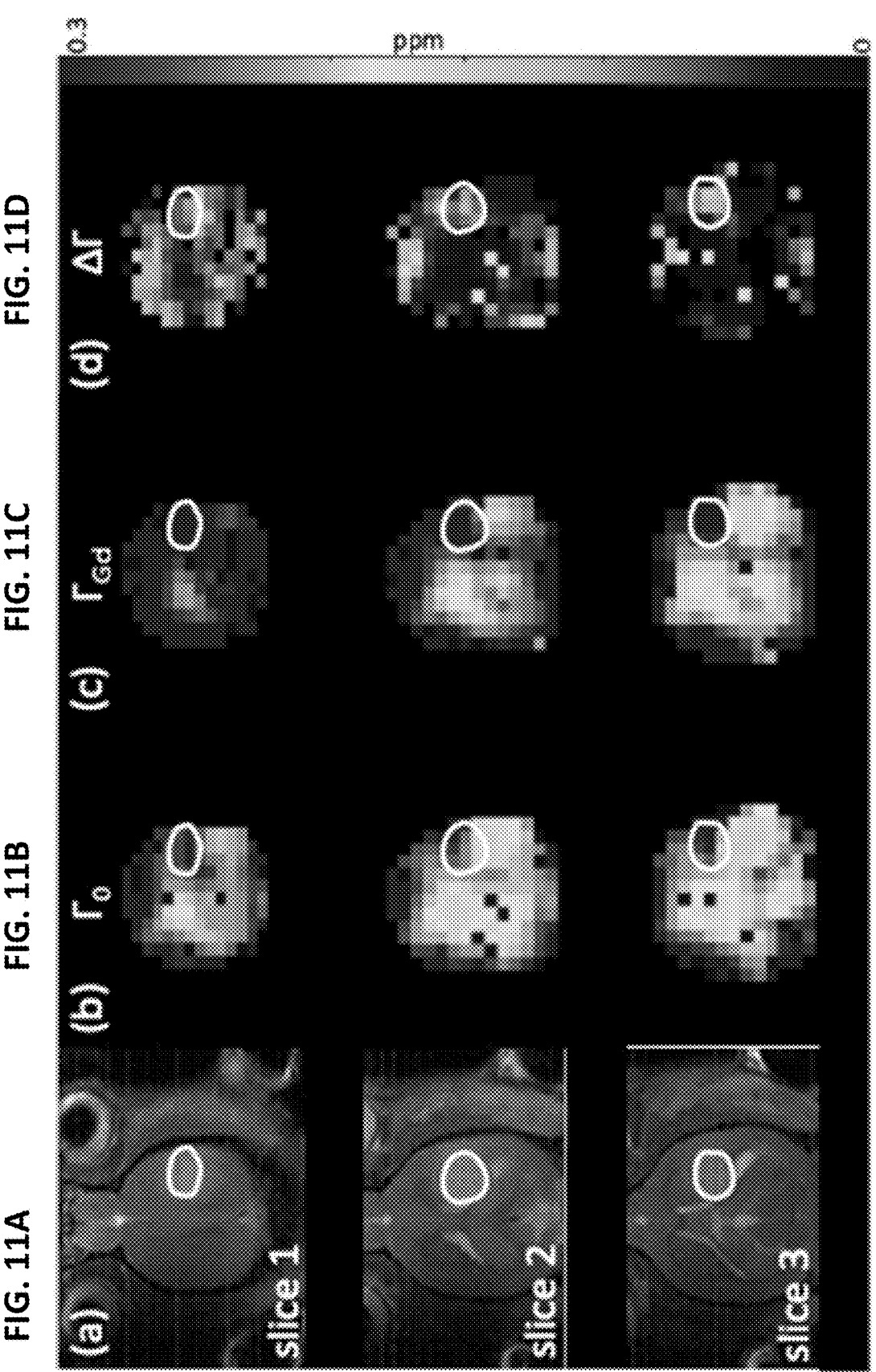
Figures 12A, 12B, 12C, 12D:
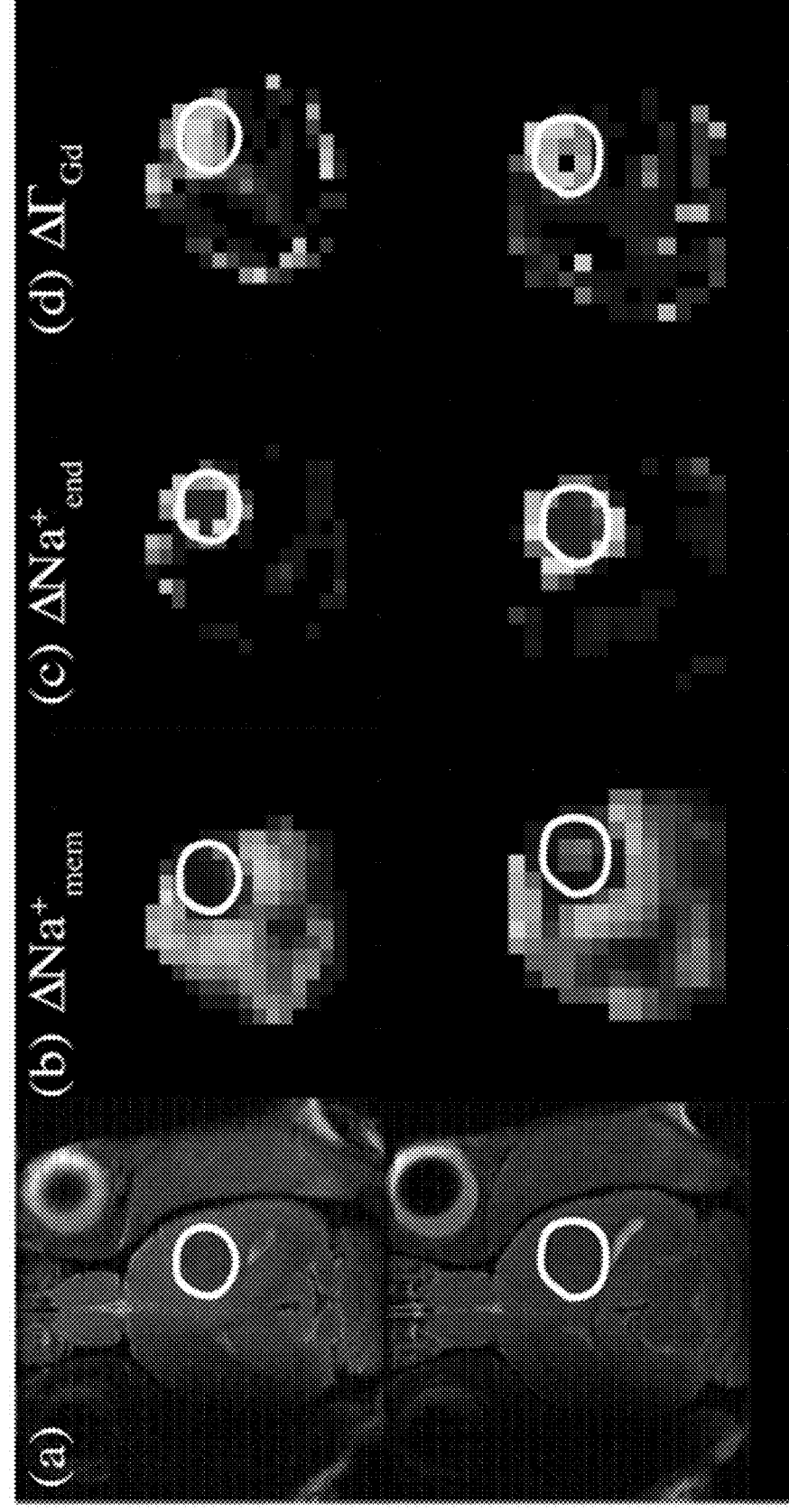

FIG. 9 depicts spatial distributions of compartmentalized $^{23}Na$ signals ($Na^+_b$, $Na^+_e$, $Na^+_i$) as well as transendothelial ($\Delta Na^+_{end}$) and transmembrane ($\Delta Na^+_{mem}$) gradients in a pair of U87 tumors, one of which was treated with sorafenib, an anti-angiogenic tyrosine kinase inhibitor that targets vascular endothelial growth factor receptor (VEGFR) and platelet-derived growth factor receptor (PDGFR). Sorafenib dosage was 0.1 g/kg body weight, dissolved in dimethylsulfoxide (DMSO) for the treated animal, whereas the untreated control received an equivalent dose of pure DMSO. Daily treatment began on day 9 post-tumor-inoculation, and imaging was performed an additional 6 days after. Sorafenib treatment clearly retarded the growth rate of the tumor. The alterations in $Na^+$ distribution (elevated Na b and $\Delta Na^+_{end}$, with decreased $Na^+_e$ and $\Delta Na^+_{mem}$) were also confined to a smaller region for the treated tumor. This demonstrates the utility of the sodium imaging method for monitoring therapeutic efficacy of drugs.

Figures 10A, 10B, 10C, 10D, 10E, 10F:
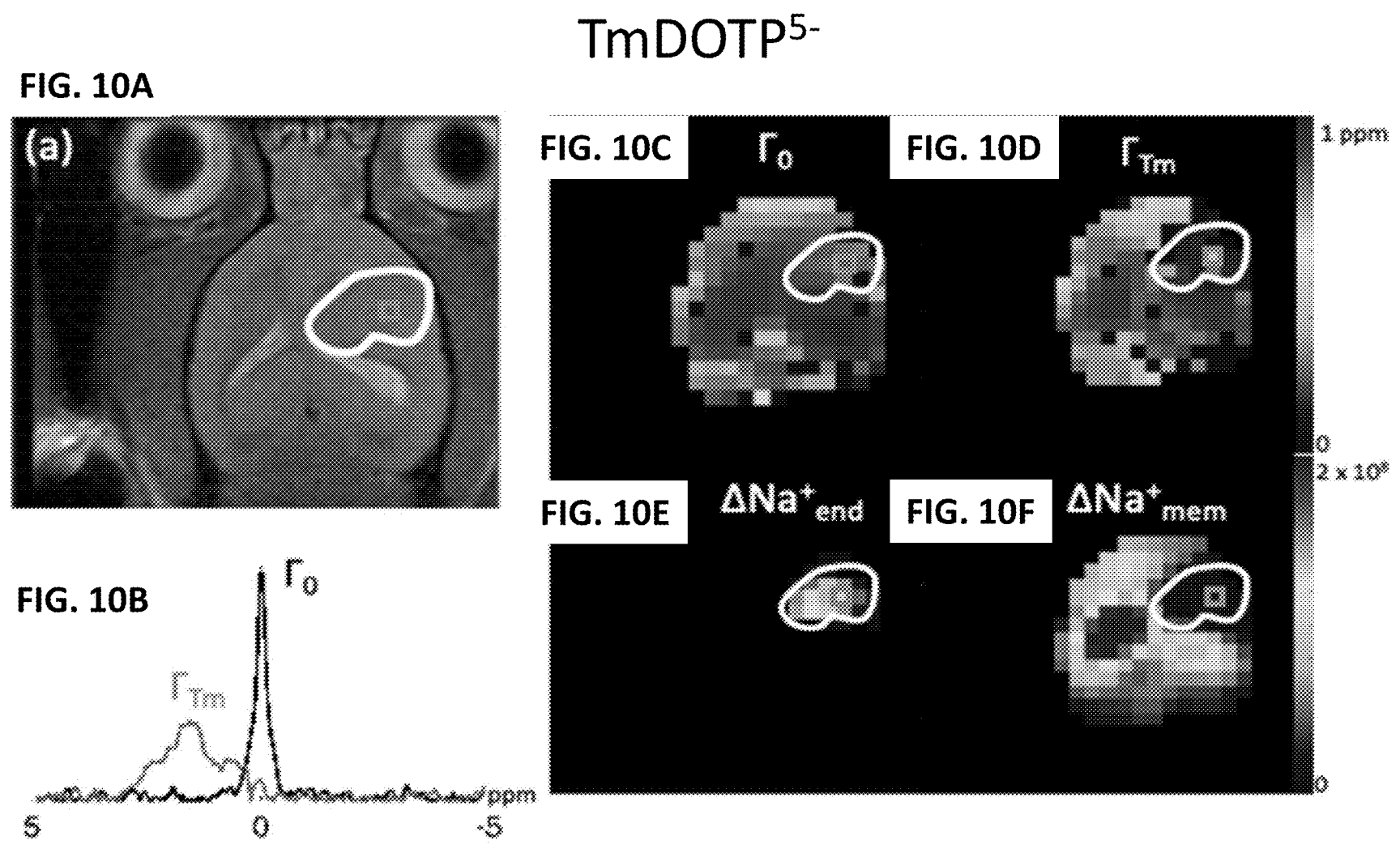

FIGS. 10A-10F depicts demonstration of $^{23}Na$-MRSI line broadening in brain tumors using TmDOTP$^{5-}$. (FIG. 10A) $^1H$ MRI of a brain slice from a U87-bearing rat is shown, overlaid with $^{23}Na$-MRSI (red). $^{23}Na$ linewidth maps (FIG. 10B) before ($\Gamma_0$) and (FIG. 10C) after TmDOTP$^{5-}$ ($\Gamma_{Tm}$) are displayed. FIGS. 10C-10F illustrates images according to certain embodiments of the disclosure. While broadening can be appreciated throughout the brain, it is most prominent within the tumor, indicative of greater TmDOTP$^{5-}$ accumulation within that region. However, the $^{23}Na$ linewidth analysis by TmDOTP$^{5-}$ is confounded by its high $^{23}Na$ shiftability. This peak separation in vivo overestimates the full-width at half-maximum (FWHM) calculations and exaggerates the measured $^{23}Na$ linewidths. This makes TmDOTP$^{5-}$ a less effective biosensor for $^{23}Na$ linewidth in vivo. However GdDOTP$^{5-}$ is able to broaden $^{23}Na$-MRSI spectra to a similar extent as TmDOTP$^{5-}$ ($\beta_c$(TmDOTP$^{5-}$) ~$\beta_c$(GdDOTP$^{5-}$)), but without inducing $^{23}Na$ shift differences between compartments [$s_c$(TmDOTP$^{5-}$)>$s_c$(GdDOTP$^{5-}$)].

FIGS. 11A-11D depicts multi-slice demonstration of $^{23}Na$-MRSI line broadening in glioma models using GdDOTP$^{5-}$. (FIG. 11A)$^1H$ MRI of a brain slice from a U87-bearing rat is shown, overlaid with $^{23}Na$-MRSI (red). $^{23}Na$ linewidth maps (FIG. 111B) before ($\Gamma_0$) and (FIG. 11C) after GdDOTP$^{5-}$ ($\Gamma_{Gd}$) are displayed, resulting in a (FIG. 11D) $^{23}Na$ linewidth broadening map ($\Delta\Gamma$) across several slices. Slice 1 is most superficial, and slice 3 is the deepest. The tumor outline is depicted in white in all columns. While broadening can be appreciated throughout the brain, it is most prominent within in the tumor, indicative of greater GdDOTP$^{5-}$ accumulation within that region.

FIGS. 12A-12D depicts multi-slice (FIG. 12A) demonstration of correlations between changes in the (FIG. 12B) transmembrane ($\Delta Na^+_{mem}$) and (FIG. 12C) transendothelial ($\Delta^{Na}_+$ end), visualized following TmDOTP$^{5-}$ infusion, with (FIG. 12D)$^{23}Na$-MRSI linewidth broadening, as evidenced by GdDOTP$^{5-}$ infusion ($\Delta\Gamma_{Gd}$) in the same rat. The tumor exhibited weakened $\Delta Na^+_{mem}$ and strengthened $\Delta Na^+_{end}$, and the magnitudes of these changes correlated well with $\Delta\Gamma_{Gd}$ values. This establishes GdDOTP$^{5-}$-induced $^{23}Na$ linewidth broadening as a potential surrogate marker for the altered $Na^+$ biodistribution within tumors. Thus, in brain tumor models, TmDOTP$^{5-}$ with $^{23}Na$-NMR can separate $Na^+$ in intracellular, blood, and interstitial pools, while GdDOTP$^{5-}$ can distinguish $Na^+$ within intracellular and extracellular (i.e., blood and interstitial) pools.

8

Figure 13A:
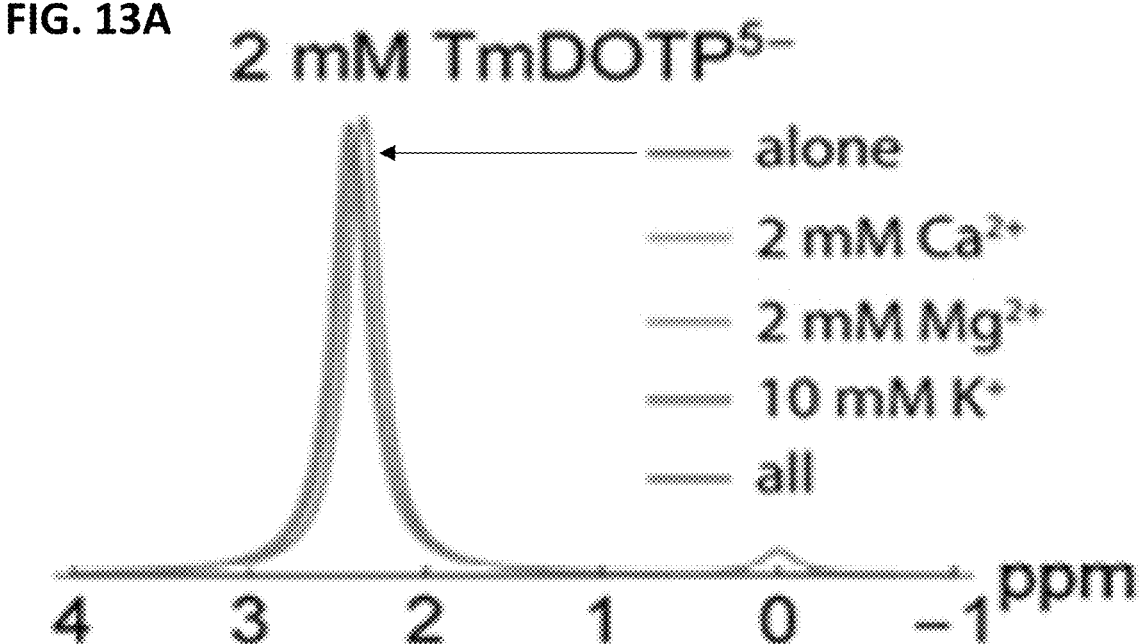
Figures 14A, 14B, 14C, 14D:
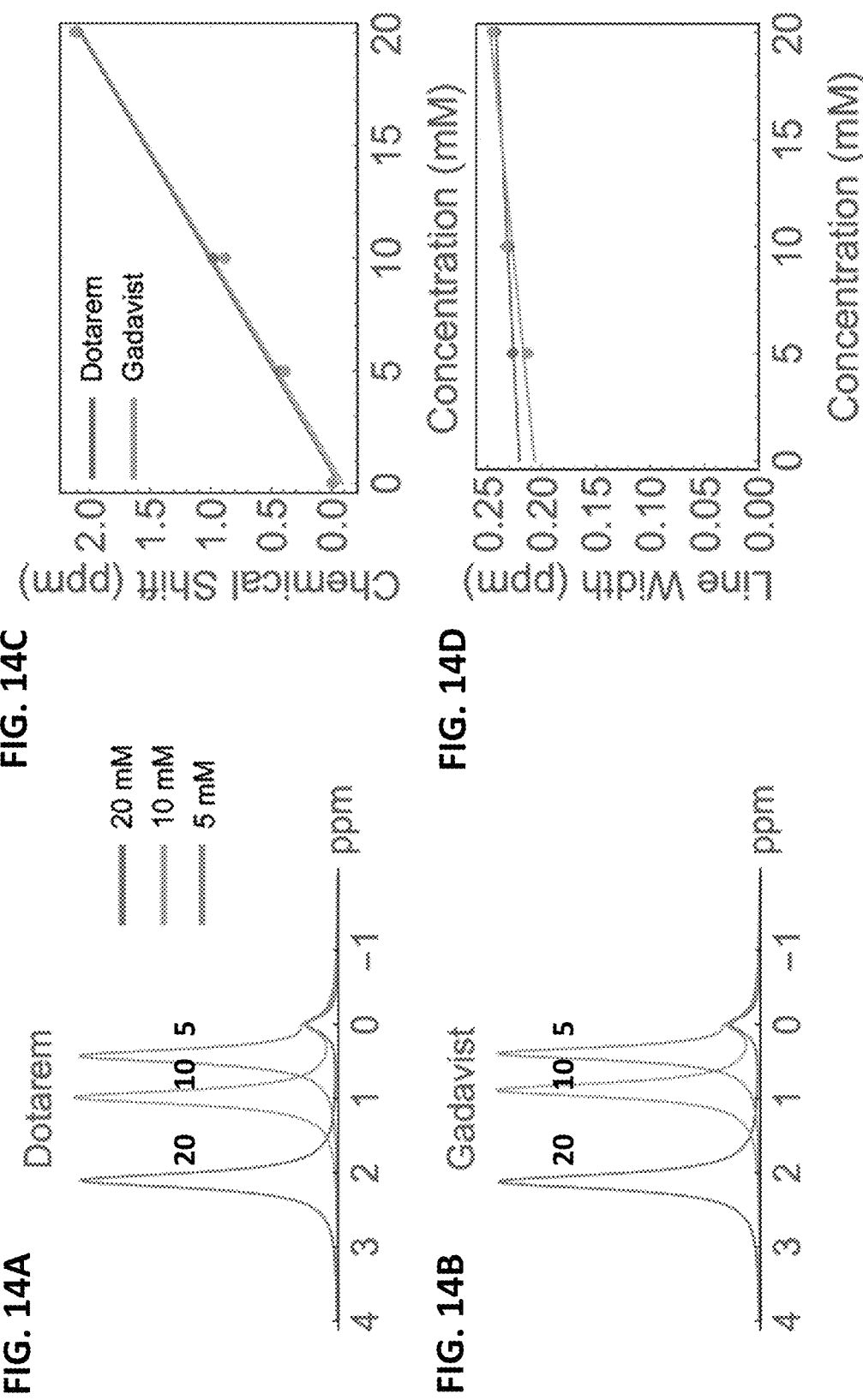

FIGS. 13A-13C depicts effect of cation competition on $^{23}Na$ chemical shift and linewidth induced by 2 mM TmDOTP$^{5-}$. (FIG. 13A)$^{23}Na$ NMR spectra for 150 mM NaCl solutions containing 2 mM TmDOTP$^{5-}$ alone, and in the presence of 2 mM $Ca^{2+}$, 2 mM $Mg^{2+}$, 10 mM $K^+$, and all three of these ions. $Ca^{2+}$, $Mg^{2+}$, and $K^+$ were introduced as the salts $CaCl_2$, $MgCl_2$, and KBr, respectively. These concentrations were all chosen to represent physiological concentrations in the interstitial space. The changes in $^{23}Na$ (FIG. 13B) chemical shift and (FIG. 13C) linewidth both were negligible, suggesting overall higher affinity for $Na^+$ given the aforementioned amounts. Chemical shift ranged between 2.433 ppm (FIG. 13B, alone) and 2.352 ppm (FIG. 13B, all), representing only a 3% change in the presence of all competing cations. Linewidth ranged between 0.2433 ppm (FIG. 13C, alone) and 0.2285 ppm (FIG. 13C, all), representing only a 6% change in the presence of all competing cations.

FIGS. 14A-14D illustrate concentration effects of Dotarem (which comprises organic acid DOTA as a chelating agent, gadolinium ($Gd^{3+}$), in form of the meglumine salt; also known as gadorate meglumine or $Gd^{3+}$2-[4,7,10-tris(carboxymethyl)-1,4,7,10-tetrazacyclododec-1-yl]acetate) and Gadavist (Gd-DO3A-butrol; also known as gadobutrol or $Gd^{3+}$2,2',2"-(10-((2R,3S)-1,3,4-trihydroxybutan-2-yl)-1,4,7,10-tetraazacyclododecane-1,4,7-triyl)triacetate) on $^{23}Na$ spectra. $^{23}Na$ spectra are displayed for concentric tubes parallel to the magnetic field, where the agent added to the outer compartment in the phantom was (FIG. 14A) Dotarem, or (FIG. 14B) Gadavist. Spectra are shown for 20 mM, 10 mM, and 5 mM, where 0 ppm corresponds to the natural, unshifted $^{23}Na$ resonance of the inner compartment to which no agent was added. The $^{23}Na$ chemical shifts display a shiftability stronger than the other $Gd^{3+}$-based agents with macrocyclic chelates.

DEFINITIONS

The instant invention is most clearly understood with reference to the following definitions.

As used herein, the singular form "a," "an," and "the" include plural references unless the context clearly dictates otherwise.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

As used in the specification and claims, the terms "comprises," "comprising," "containing," "having," and the like can have the meaning ascribed to them in U.S. patent law and can mean "includes," "including," and the like.

Unless specifically stated or obvious from context, the term "or," as used herein, is understood to be inclusive.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 (as well as fractions thereof unless the context clearly dictates otherwise).

DETAILED DESCRIPTION OF THE INVENTION

Methods for detecting sodium ion balances in vivo are described herein. Metallic ions, such as lanthanide (III) metal ions ($Ln^{3+}$) or transition (II) metal ions ($Tn^{2+}$), complexed with polyanionic macrocyclic chelates can be administered in vivo to detect differences between intracellular and interstitial sodium levels.

In certain embodiments, the lanthanide (III) metal ion comprises at least one of $La^{3+}$, $Ce^{3+}$, $Pr^{3+}$, $Nd^{3+}$, $Pm^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, $Lu^{3+}$, and so forth.

In certain embodiments, the transition (II) metal ion comprises at least one of $Mn^{2+}$, $Fe^{2+}$, $Co^{2+}$, $Ni^{2+}$, $Cu^{2+}$, and so forth.

In certain embodiments, the polyanionic macrocyclic chelate comprises at least one of $DOTA^{4-}$ (2,2',2'',2'''-(1,4,7,10-Tetraazacyclododecane-1,4,7,10-tetrayl)tetraacetic acid), $DOTP^{8-}$ (1,4,7,10-Tetraazacyclododecane-1,4,7,10-tetra(methylene phosphonate), $DOTMA^{-4}$ ((1R,4R,7R,10R-$\alpha,\alpha',\alpha'',\alpha'''$-tetramethyl-1,4,7,10 tetraazacyclododecane-1,4,7,10-tetraacetate), $NOTP^{-6}$ (1,4,7-Triazacyclononane-1,4,7-tri(methylene phosphonate), $DOTA$-$4AmP^{8-}$ (1,4,7,10-tetraazacyclododecane-1,4,7,10-tetrakis(acetamido-methyl-enephosphonate), DO3A-butrol (2,2',2''-(10-((2R,3S)-1,3,4-trihydroxybutan-2-yl)-1,4,7,10-tetraazacyclododecane-1,4,7-triyl)triacetate), and so forth.

The large negative charges on these biosensors can attract $Na^+$, and their paramagnetic metals produce chemical shifts in NMR resonance frequency. Thus, these biosensors can act as efficacious shift reagents which can produce chemical shifts in blood and interstitial $Na^+$ when infused intravenously in vivo, but not in intracellular $Na^+$ since they are barred from crossing the cell membrane. Exchange between $Na^+$ bound to these agents and free $Na^+$ in the bulk electrolyte can also produce line broadening in the $^{23}Na$ NMR signal. Both chemical shift and linewidth can also increase with agent concentration and negative charge. The concentration-dependence of these spectroscopic features of the $^{23}Na$ signals allow for minimally-invasive compartmentalization of in vivo $Na^+$.

An example of a biosensor, $TmDOTP^{5-}$ (FIG. 1A), has high shiftability (sensitivity of $^{23}Na$ chemical shift to agent concentration), and can isolate $^{23}Na$ magnetic resonance spectroscopic imaging (MRSI) signals from blood, interstitial, and intracellular compartments within tumors (e.g., gliomas) by producing respective chemical shift differences. Moreover, this MRSI method can image the effectiveness of cancer therapies like sorafenib. Both $TmDOTP^{5-}$ and $GdDOTP^{5-}$ have high broadening potentials (sensitivity of linewidth to agent concentration), and infusion of the latter demonstrated considerable linewidth broadening within gliomas.

Experiment #1

In Vitro Studies for Mechanistic Separation of $^{23}Na$ Peaks

Figures 1A, 1B, 1C:
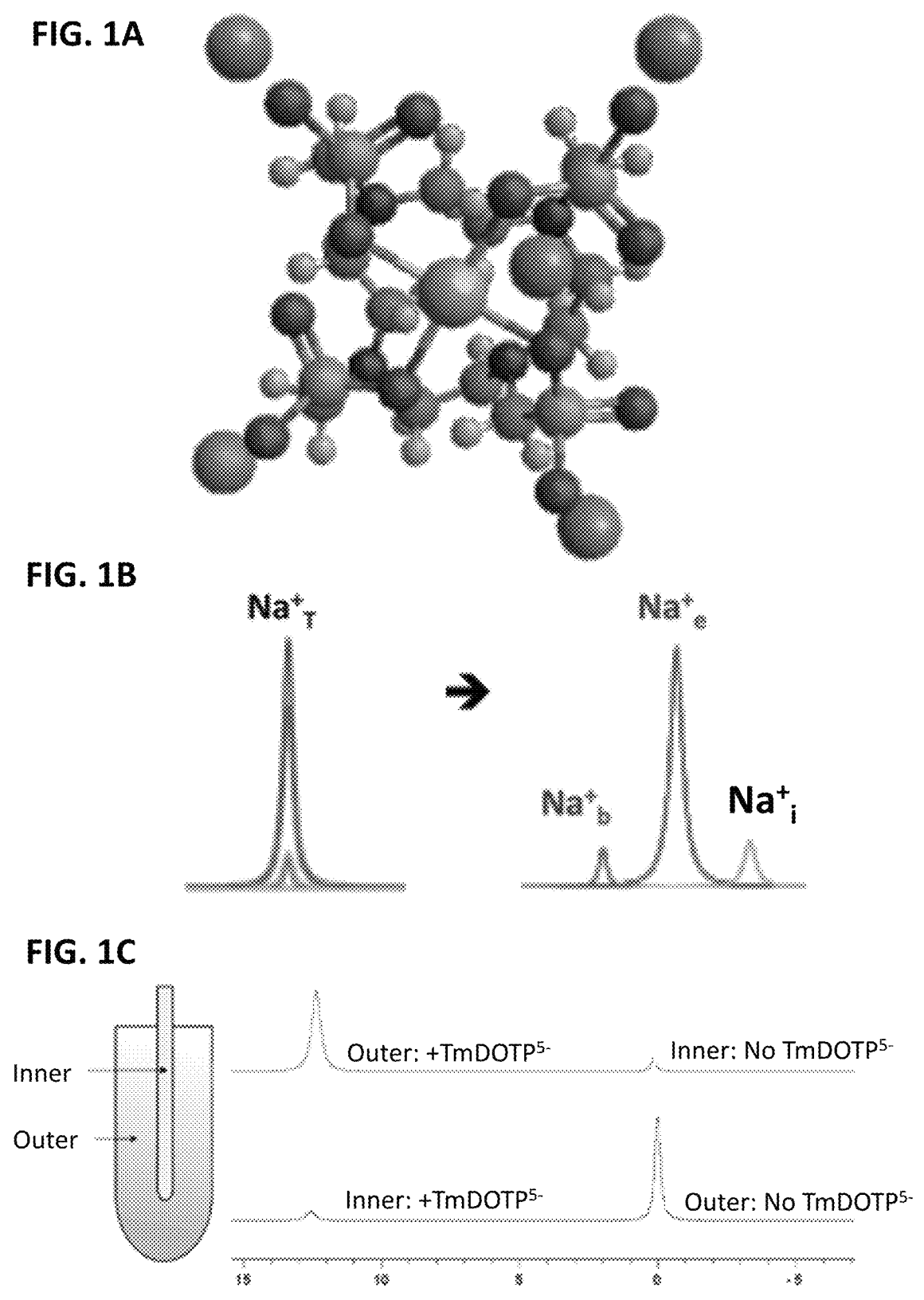
Figures 1D, 1E, 1F, 1G:
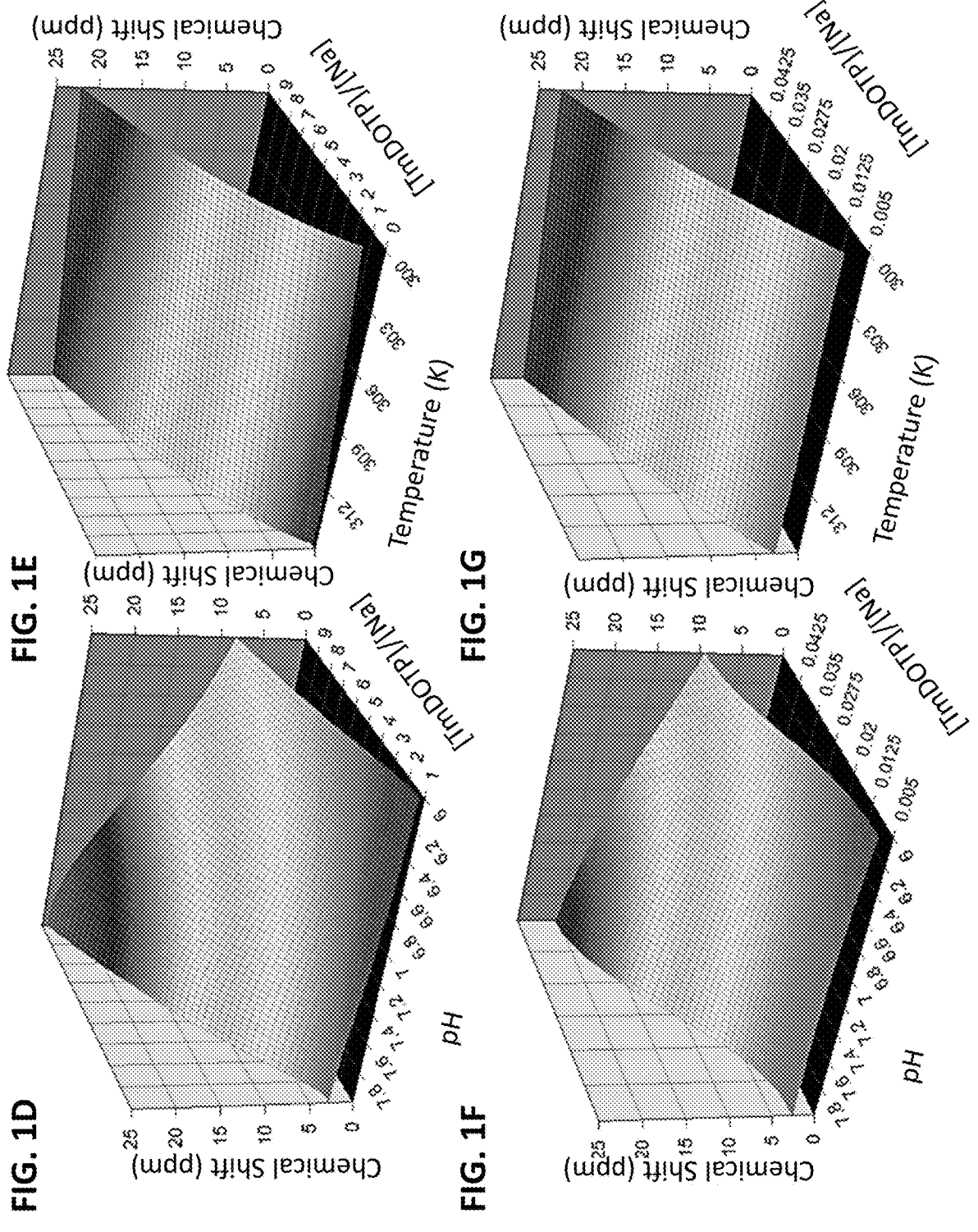

The goal of these studies was to separate the total $Na^+$ signal ($Na^+_T$) into distinct signals for blood ($Na^+_b$), interstitial ($Na^+_e$), and intracellular ($Na^+_i$) pools (FIG. 1). The shifting mechanism induced by exogenous $TmDOTP^{5-}$ and endogenous biological factors on the $^{23}Na$ chemical shift in vitro is depicted in FIGS. 1C-1G. A two-compartment coaxial cylinder NMR tube setup in vitro was used to mimic $Na^+$ in interstitial/intracellular pools. The inner (smaller) and outer (larger) compartments both contained 150 mM NaCl while the latter also contained $TmDOTP^{5-}$ at various concentrations. The setup was subjected to several different pH and temperature conditions. The inner compartment, which lacked $TmDOTP^{5-}$ to represent the intracellular space in vivo, produced a small but unshifted $^{23}Na$ peak at 0 ppm. The larger $^{23}Na$ peak was shifted downfield by $TmDOTP^{5-}$, with the difference in peak integrals stemming from different compartment volumes. The feasibility of this approach to quantify $Na^+$ signals from different compartments is demonstrated by switching the contents of the compartments and then repeating the above measurements.

In vitro $^{23}Na$ spectra revealed that the chemical shift was most sensitive to [$TmDOTP^{5-}$] changes, compared to pH and temperature variations (FIG. 1C). The $^{23}Na$ shiftability for $TmDOTP^{5-}$ $s[paraCA''^-]=2.1$ ppm/mM was $11.1\times$larger than the shiftability for pH ($s_{pH}=0.25$ ppm/pH unit) and $92.3\times$larger than the shiftability for temperature ($s_T=0.03$ ppm/° C.). This means that addition of 1.1 mM $TmDOTP^{5-}$ would induce a ~3 ppm shift in the $^{23}Na$ peak. Conversely, a maximal change of 0.4 in pH units, which is observed between normal and tumor tissues, would induce only a ~0.1 ppm $^{23}Na$ shift. A similar $^{23}Na$ shift by temperature would require a 3.3° C. change, which is unlikely in vivo. Based on the pH and temperature ranges observed in vivo (including tumors), the effect from [$TmDOTP^{5-}$] dominates the $^{23}Na$ chemical shift by 95%. Therefore, [$TmDOTP^{5-}$] is several orders of magnitude more sensitive in shifting the $^{23}Na$ resonance than typical in vivo factors. Furthermore, the $^{23}Na$ shiftability arising from [$TmDOTP^{5-}$] and pH/temperature effects is much larger than $T_2$ broadening from $TmDOTP^{5-}$ (FIG. 1C). Consequently, $^{23}Na$ spectra displayed dependence mostly on [$TmDOTP^{5-}$] (FIGS. 1D-1E). However, for in vivo scenarios the ranges shown for pH (2 full pH units) and temperature (15° C. interval) are overestimated, and where [$Na^+$] far exceeds [$TmDOTP^{5-}$] based on prior experiments. In blood and interstitial spaces, [$Na^+$] is ~30-100×greater than [$TmDOTP^{5-}$]. This suggests that the relative amount of $TmDOTP^{5-}$ (FIGS. 1F-1G) is the primary factor affecting $^{23}Na$ chemical shift.

In Vivo Separation of $^{23}Na$ Peaks Indicates Compartmentalized $Na^+$ Pools

Interrogating individual voxels in the brain before and after $TmDOTP^{5-}$ administration (~1 μmol/g body weight (BW)) revealed clear $^{23}Na$ signal separation, although to varying extents depending on the degree of $TmDOTP^{5-}$ extravasation from blood to the interstitial space. $^{23}Na$-MRSI data overlaid on $^1H$-MRI anatomy of rat brains bearing U251 tumors showed spectra in tumor and healthy tissue voxels (FIG. 2A), with candidate voxels inside (FIG. 2B) and outside (FIG. 2C) the tumor before and after $TmDOTP^{5-}$. Before $TmDOTP^{5-}$ delivery, there was a single $^{23}Na$ peak at 0 ppm corresponding to $Na^+_T$, observed ubiquitously both inside and outside the tumor. Upon $TmDOTP^{5-}$ delivery, compartmental $^{23}Na$ peak separation was achieved. Within the tumor, the compromised BBB permitted greater $TmDOTP^{5-}$ extravasation and accumulation in the interstitial space, explicitly yielding three separate $^{23}Na$ peaks emerging from the original single $^{23}Na$ resonance. Each peak was associated with a compartment, with $Na^+_i$ being the unshifted peak (0 ppm) because $TmDOTP^{5-}$ could not enter the intracellular compartment, and other peaks exhibiting $TmDOTP^{5-}$-dependent shifts. In the tumor, the most-shifted peak was $Na^+_b$ because the blood compartment had the largest $TmDOTP^{5-}$, which was corroborated by removing blood samples from the animal and observing the same chemical shift in vitro (FIG. 2D). In the tumor, the intermediate peak in the middle corresponded to the interstitial $Na^+_e$ resonance (FIG. 2B). The splitting was also evident outside of the tumor (i.e., in healthy tissue) where $TmDOTP^{5-}$ extravasated to a much lesser extent compared to tumor tissue (FIG. 2C). The $Na^+_b$ peak was still most-shifted, whereas the $Na^+_i$ and $Na^+_e$ peaks were less discernible. When there was significant overlap between adjacent peaks, instead of peak integrals the peak amplitudes were used to discriminate signals. The shifted bulk $Na^+_e$ peak in healthy tissue confirmed that whatever degree of $TmDOTP^{5-}$ extravasation occurred was sufficient to affect the interstitial $^{23}Na$ signals, albeit less pronounced than tumoral $Na^+_e$. The unshifted $Na^+_i$ resonance was still at 0 ppm, but partially eclipsed by the bulk $Na^+_e$ peak. These same patterns inside/outside the tumor were observed throughout the brain.

FIGS. 3A-3B display data from representative rats bearing RG2 (FIG. 3A) and U87 (FIG. 3B) tumors, with the array of $^{23}Na$-MRSI data overlaid on top of the $^1H$-MRI anatomy. The spectra from individual voxels placed throughout the brain confirmed only one $^{23}Na$ peak prior to infusion (FIGS. 3A-3B), corresponding to $Na^+_T$, but upon $TmDOTP^{5-}$ infusion the single peak separated into two additional $^{23}Na$ peaks (FIGS. 3A-3B).

Prior to $TmDOTP^{5-}$ infusion (FIGS. 3A-3B) ventricular voxels [voxels (1) and (2) in FIGS. 3A-3B] exhibited predominantly Lorentzian lineshapes characterized by a single $T_2$, while those in the normal brain [voxels (5) and (6) in FIGS. 3A-3B] and tumor [voxels (3) and (4) in FIGS. 3A-3B] displayed super-Lorentzian lineshapes indicative of multiple $T_2$ values. This was because the ventricles are comprised almost entirely of cerebrospinal fluid (CSF), in which all $Na^+$ ions are in aqueous media, whereas some $Na^+$ ions in tissue can be bound. These observations agreed with prior $^{23}Na$-MRI results.

Administration of $TmDOTP^{5-}$ resulted in the emergence of multiple $^{23}Na$ peaks (FIGS. 3A-3B), particularly within the tumor. However, the downfield shifts seen in healthy tissue suggested the paramagnetic effects of $TmDOTP^{5-}$ were detectable, albeit not as clear as the tumor tissue. Most shifted peak are sufficiently far from the other two peaks present and attributed it to only $Na^+_b$, with and integral $$\left(\int_{-0.25\,ppm}^{+0.25\,ppm}Na^+_b\right)$$

reflecting the blood sodium concentration $[Na^+]_b$.
Likewise, $$\int_{-0.15\,ppm}^{+0.15\,ppm}Na^+_e \quad and \quad \int_{-0.1\,ppm}^{+0.1\,ppm}Na^+_i$$

measured $[Na^+]_e$ and $[Na^+]_i$, respectively, centered at their respective peak positions. Tumor voxels [voxels (3) and (4) in FIGS. 3A-3B] exhibited spectra where the three peaks were most notably present. Thus, the chemical shifts of the $Na^+_b$, $Na^+_e$, and $Na^+_i$ peaks can be respectively placed at the same peak positions. Shifts of this nature were evident throughout the entire depth of the brain for both animals. Ventricular voxels [voxels (1) and (2) in FIGS. 3A-3B] displayed only one Lorentzian peak shifted to the same extent as $Na^+_e$ in healthy tissue voxels [voxels (5) and (6) in FIGS. 3A-3B], albeit in the latter with super-Lorentzian lineshape. These shifts coincided because CSF and the interstitial space are physically in contact with unrestricted exchange of aqueous $Na^+$. Given the shiftability s[para-$CA^{n-}$] is 2.77 ppm/mM measured in vitro (FIGS. 1A-1G), the tumor vasculature contained no more than 0.7 mM $TmDOTP^{5-}$ based on the range of shifts observed. Since the blood $^{23}Na$ signal experienced the greatest shift (FIG. 2D), the (interstitial) tissue therefore encountered even less $TmDOTP^{5-}$, in agreement with prior observations.

In Vivo Depiction of Transmembrane and Transendothelial $Na^+$ Gradients

Integration of compartmentalized $^{23}Na$ spectra (FIGS. 2A-2D and 3A-3B) generated spatial maps which depicted relative $[Na^+]$ in each compartment from which the transmembrane $(\Delta Na^+_{mem}=\int Na^+_e \int Na^+_i)$ and transendothelial $(\Delta Na^+_{end}=\int Na^+_b - \int Na^+_e)$ gradient maps could also be calculated, as shown in FIG. 4 for multiple axial slices from a rat brain bearing an RG2 tumor. This 3D high-resolution demonstration of the in vivo $Na^+$ biodistribution divulged spatial heterogeneity, where the relative $[Na^+]$ of each compartment is a function of the compartment volume and the amount of $Na^+$ in that compartment. It should be noted that $TmDOTP^{5-}$ extravasation under current conditions was sufficient to observe paramagnetic effects even in healthy brain tissue, and as shown in the $T_2$ maps and concomitant $\Delta R_2$ map (given by the difference between inverse $T_2$ maps obtained after and before $TmDOTP^{5-}$ infusion) for RG2 (FIG. 4) and U87 tumors. While $\Delta R_2$ can generally depict the difference between $[TmDOTP^{5-}]$ in healthy and tumor tissues, it cannot separate $[TmDOTP^{5-}]$ in blood and interstitial compartments within the tumor. Therefore the $\Delta R_2$ map cannot fully quantify these separately, while $^{23}Na$-MRSI spectra can separate these two signals.

There was markedly increased $\int Na^+_b$ in the tumor, which was not observed elsewhere in normal brain. There was also high degree of heterogeneity within the tumor. The $\int Na^+_e$ map revealed the largest values in the ventricles (CSF) and smaller values in the tumor with a slight extent of heterogeneity. Outside the tumor, the bulk peak occurred in the integration band for $Na^+_e$. The $\int Na^+_i$ map unsurprisingly showed values that were about one order of magnitude lower throughout the brain compared to the $\int Na^+_b$ and $\int Na^+_e$ maps, since $[Na^+]_i$ (~10 mM) is an order of magnitude smaller than $[Na^+]_b$ and $[Na^+]_e$ (~150 mM). Furthermore, the $\int Na^+_i$ values were not significantly different between the tumor and healthy tissue.

The $\Delta Na^+_{mem}$ values in the tumor were significantly lower compared to the healthy tissue (p<0.05) and the map displayed a similar level of heterogeneity as the $\int Na^+_e$ map, suggesting that $\Delta Na^+_{mem}$ is driven primarily by the decrease in $Na^+_e$. Ventricular voxels still showed high values in $\Delta Na^+_{mem}$, indicating the large magnitude of $Na^+_e$ in CSF. Likewise, the significant elevation of $\Delta Na^+_{end}$ in the tumor was driven primarily by the $Na^+_b$ increase, and $\Delta Na^+_{end}$ values were significantly larger in the tumor compared to healthy tissue (p<0.05). This feature was more pronounced in superficial regions of the brain because draining veins run vertically down from cortical surface to white matter and some of these blood vessels are perpendicular to the main static magnetic field, thereby enhancing bulk magnetic susceptibility effect on surrounding tissue, which has been reported in vitro. This phenomenon is similar to blood oxygenation level-dependent functional MRI contrast mechanisms. For both $\Delta Na^+_{mem}$ and $\Delta Na^+_{end}$ gradients, statistical significance was achieved even after excluding ventricle values. These patterns could also be visualized by looking at slice projections of the compartmental and gradient values for the same RG2-bearing animal along a constant coronal position (FIGS. 5A-5C). For the RG2 tumor, the tumoral increases in $Na^+_b$ and $\Delta Na^+_{end}$ were highest superficially (slices 1-4). Conversely, peritumoral values of $Na^+_e$ and $\Delta Na^+_{mem}$ increased with depth up to a point in the middle of the brain (slices 3-4) before diminishing. Intratumoral $Na^+_e$, however, did not vary significantly with depth. $Na^+_i$ also decreased inside the tumor but not significantly. The $\Delta Na^+_{mem}$ and $\Delta Na^+_{end}$ respectively behaved similarly to $Na^+_b$ and $Na^+_e$ since they were the primary drivers of those gradients. Similar observations were made for U87 tumors regarding $Na^+$ in each compartment and the corresponding gradients.

Throughout the entire cohort of rats (FIGS. 6A-6B), the mean $\int Na^+_b$ values were larger and mean $\int Na^+_e$ values were lower in the tumor compared to normal tissue. These trends were significant in RG2 ($p<0.005$) and U87 ($p<0.05$) tumors while there was no significant difference in $\int Na^+_i$ for all three tumors (FIG. 6A). Identical trends were also observed in $\Delta Na^+_{end}$ and $\Delta Na^+_{mem}$, and significantly so in RG2 ($p<0.005$) and U87 ($p<0.05$) tumors. Moreover, $\Delta Na^+_{end}$ was significantly stronger in RG2 and U87 tumors compared to U251 ($p<0.05$) (FIG. 6B).

Since a strengthened $\Delta Na^+_{end}$ is indicative of impaired vascular integrity, $^1$H-DCE-MRI was employed to reliably image vascular function within the tumor core. Of the four parameters which can be obtained by fitting $^1$H-DCE-MRI data from a two-compartment exchange model, the volume transfer constant ($K^{trans}$) and plasma volume fraction ($v_p$), as shown in FIG. 6C, both followed the trends of $\Delta Na^+_{end}$ across tumor types: in RG2 and U87 tumors compared to U251, there was a significant difference ($K^{trans}$: $p<0.005$ and $v_p$: $p<0.05$; for plasma flow rate ($F_p$) and interstitial volume fraction ($v_e$)). Although significance was marginal for $F_p$, the mean values followed suit. The $^1$H-DCE-MRI data displayed regions of low $F_p$ and larger $v_e$ within an exemplary slice of a U251 tumor, indicative of a necrotic core, which RG2 and U87 animals lacked. Reduced $\Delta Na^+_{end}$ in U251 tumor (FIG. 6B) could be a marker of necrosis presence as evidenced by lower $K^{trans}$ and higher $v_p$ in the core of U251 tumors. These results suggest that U251 tumors would have lower tissue and blood oxygenation compared to RG2 and U87 tumors. Additionally, beyond the core of U251 tumors $v_e$ on average was smaller than $v_p$, indicating a high degree of tumor angiogenesis. These findings further substantiate the $\int Na^+_b$ and $\Delta Na^+_{end}$ results derived from the $^{23}$Na-MRSI studies. Given $v_e$ and $v_p$ heterogeneity, the minor $^{23}$Na peaks downfield of 2 ppm was attribute to agent pooling from ineffective agent clearance.

FIGS. 7A-7C shows $\int Na^+_b$, $\int Na^+_e$, $\int Na^+_i$, $\Delta Na^+_{end}$, and $\Delta Na^+_{mem}$ maps across all tumor cell lines (RG2, U87, U251). The trends seen previously pervaded all animals, but to varying degrees based on the tumor type. The $\int Na^+_b$ elevation, and concomitant $\Delta Na^+_{end}$ strengthening, were most pronounced for the RG2 tumor, followed by U87 and then U251. Likewise, the decrease in $\int Na^+_e$ and weakening of $\Delta Na^+_{mem}$ followed the same order for the tumors. In all tumors, $Na^+_b$ and $Na^+_e$ patterns respectively drove the behaviors of $\Delta Na^+_{end}$ and $\Delta Na^+_{mem}$.

Selected Comments

The results enabled comparisons of $Na^+$ physiology and distributions among RG2, U87, and U251 gliomas. Both U87 and U251 are human-derived cell lines, whereas RG2 is derived from rat glioma. Experimentally the U251 tumor is most heterogeneous, since U251 cells grow erratically and anisotropically compared with RG2 and U87 cells. Additionally, the U251 tumor is more invasive and infiltrative than U87, and U251 cells display greater necrosis, expression of hypoxia-inducible factor 1-alpha (HIF1α) and of Ki67, indicating higher rates of proliferation. U251 cells also test positive for glial fibrillary acidic protein (GFAP) and vimentin, and exhibit neovascularization and angiogenesis. U87 cells are also positive for vimentin and exhibit significant angiogenesis but do not develop necrosis. Neither U251 nor U87 exhibits endothelial proliferation, a common hallmark of human-derived GBM cell lines. The RG2 tumor exhibits invasiveness and induces BBB disruption, producing edema surrounding the tumor where pericytes help promote angiogenesis to increase permeability of the tumor vasculature. These data concur with the findings. It was observed that the negative correlation between the transmembrane and transendothelial gradients were strong in the RG2 and U87 lines but weak for U251. The increase of the transendothelial gradient nearly matched the decrease of the transmembrane gradient in U87 tumors, and exceeded in RG2, which matched behavior regarding BBB permeability. Higher density of blood vessels or higher blood volume would explain higher $^{23}$Na signal but not necessarily higher $Na^+$ concentration in the blood. Although the blood vessels are leaky to gadolinium ($Gd^{3+}$) ions, the elevated transendothelial gradient suggests that the BBB is impermeable to $Na^+$, which is well known.

Alkylating chemotherapy agents modify DNA bases of cancer cells with an alkyl group to restrict the replication process. For example, temozolomide (TMZ) achieves cytotoxicity by methylating the $O^6$ position of guanine. $O^6$-methylguanine-DNA-methyltransferase (MGMT) is a DNA repair enzyme, which ordinarily repairs the naturally occurring DNA lesion $O^6$-methylguanine back to guanine and prevents mistakes during DNA replication and transcription. Unfortunately, MGMT can also protect tumor cells by the same process and neutralize the cytotoxic effects of agents like TMZ. If the MGMT gene is silenced by methylation in tumor cells (i.e. MGMT-negative or MGMT-methylated), its DNA repair activity is diminished and the tumor's sensitivity to chemotherapy is amplified. This suggests that MGMT-positive tumor cells become resistant to chemotherapy, and therefore would possess a depolarized $V_m$ due to its proliferative state.

A recent study demonstrated higher MGMT mRNA expression for RG2 compared to U87. Another study showed that the 50% inhibition concentration ($IC^{50}$) of TMZ for U87 and U251 cells are comparable. Together, these suggest that RG2 is most resistant to chemotherapy presumably due to its augmented proliferative/replicative state, and hence a depolarized $V_m$. These observations partially agree with the results, where RG2 and U87 tumors maintain a depolarized $V_m$ for their proliferative/replicative state to persist.

Selected Study Highlights

In vitro $^{23}$Na shifts were most dependent on [TmDOTP$^{5-}$] given its high shiftability ($s_{[paraCAn-]}$=2.77 ppm/mM), whereas shiftability due to pH and temperature effects were negligible within physiological ranges ($s_{pH}$=0.25 ppm/pH unit; $s_T$=0.03 ppm/° C.). The maximum pH difference between glioma and brain tissue is ~0.4 pH units whereas temperature differences of ~0.5° C. are extremely unusual in the brain. Under these extreme conditions, the respective $^{23}$Na shift variations caused by pH and temperature would be 0.1 ppm and 0.015 ppm, respectively. Meanwhile, TmDOTP$^{5-}$ can reach in vivo concentrations close to 1-2 mM in blood and interstitial spaces which would cause $^{23}$Na shifts of 2.8-5.5 ppm. While [TmDOTP$^{5-}$] was not calculated in each voxel, the sodium shiftability was specifically used to discern that the most shifted peaks were from the blood and interstitial (or CSF) compartments, respectively.

Given observed $^{23}$Na linewidths in vivo on the order of ~0.4 ppm, TmDOTP$^{5-}$ concentration effects dominate the shifting effect (96-98%). Therefore, $^{23}$Na shiftability can be considered a univariate function of [TmDOTP$^{5-}$] in vivo.

Upon translation of the present in vitro results to in vivo situations, certain confounding factors must be addressed. In the interstitial space, there are additional cations such as calcium (Ca$^{2+}$), magnesium (Mg$^{2+}$) and K$^+$ which will also bind to anionic contrast agents like TmDOTP$^{5-}$. However, physiologically their concentrations are low compared to Na$^+$. The effect of cationic competition in vitro was assessed (FIGS. 13A-13C) and negligible changes in $^{23}$Na chemical shift and linewidth at typical in vivo concentrations were observed for these cations. Therefore, without wishing to be limited by any theory, ones do not expect the presence of these cations in vivo to affect the general findings. Additionally, there is a contribution to the chemical shift from bulk magnetic susceptibility (BMS) changes brought about by TmDOTP$^{5-}$ in addition to the hyperfine shifts induced by interactions with Na$^+$. Experiments were performed on different DOTP$^{8-}$ salts in phantoms parallel and perpendicular to the main magnetic field B$_0$, and also spherical phantoms in which there was no BMS contribution. Only a small portion (~2%) of the total chemical shift for TmDOTP$^{5-}$ was due to BMS arising due to anisotropy of the paramagnetic susceptibility, and the remainder was the hyperfine shift. However, this is not the case for GdDOTP$^{5-}$ which was dominated by BMS effect. Therefore, in vivo BMS contributions will also not significantly affect the TmDOTP$^{5-}$ results, but the BMS contributions themselves could also be used for imaging sodium compartments with GdDOTP$^{5-}$.

These observations enabled attributing individual $^{23}$Na peaks to specific in vivo pools for blood, interstitial and intracellular spaces arising from compartmental differences in [TmDOTP$^{5-}$] upon intravenous administration (~1 μmol/g). The $^{23}$Na shifts in tumor tissue (~0.5-1 ppm) were more conspicuous compared to peritumoral tissue, but lower than in blood (~2 ppm), suggesting larger [TmDOTP$^{5-}$] in the blood compartment. Additionally, the blood and interstitial peaks were separated by ~1.5 ppm, much larger than their linewidths (~0.4 ppm), indicating minimal cross-compartmental contributions.

Integrating the separated $^{23}$Na peaks enabled spatial mapping of Na$^+$ compartments and gradients in vivo. In the tumor, compared to normal tissue, the transendothelial Na$^+$ gradient was stronger and the transmembrane Na$^+$ gradient was weaker due to elevated blood and decreased interstitial $^{23}$Na signals. Current agent concentration does not affect the Na$^+$ gradients, simply the chemical shift position of the $^{23}$Na peak for each compartment. However, an order of magnitude higher agent concentration would affect the estimation of the Na$^+$ gradients due to amount of Na$^+$ ions co-infused. The enhanced $^{23}$Na blood signals in tumors complied with dynamic $^1$H-DCE-MRI scans based on Gd$^{3+}$ uptake, which revealed a higher degree of vascularity in RG2 and U87 tumors. Interstitial Na$^+$ signal in the ventricles was also very high due to the presence of the agent in CSF. However, ventricular $^{23}$Na peaks were Lorentzian because CSF contains primarily aqueous Na$^+$ and thus a single T$_2$ component, whereas tissue $^{23}$Na peaks appeared super-Lorentzian because semi-solid Na$^+$ binding in tissue resulted in multiple T$_2$ components.

Comparisons with Previous Work

The present in vitro data improve upon earlier attempts at quantifying $^{23}$Na shiftability using paraCA$^{n-}$ versus many parameters like pH, temperature and other cations. However, the findings focused more on characterizing the dependence on each parameter (linear, sigmoidal, etc.) rather than considering relevant in vivo conditions. The $^{23}$Na shiftability model does not require assessing the effects of cationic competition for attraction to TmDOTP$^{5-}$ because other cations are not present in blood and/or interstitial spaces in concentrations comparable to Na$^+$.

Prior in vivo $^{23}$Na-NMR spectroscopy studies utilizing TmDOTP$^{5-}$ in the brain failed to elucidate spatial information, and instead only focused on acquisition of either global data or localized voxels. The findings reported two broadened peaks, an unshifted intracellular peak and a very broad shifted extracellular (i.e., blood and interstitial) peak. Based on two peaks over limited spatial regions, these studies could not comment specifically on the spatial distribution of transmembrane gradient. Furthermore, the blood $^{23}$Na signal was not separated so the transendothelial gradient could not be assessed. The shifting capability of TmDOTP$^{5-}$ for separating $^{23}$Na resonances in tumor tissue was demonstrated in situ, but still at a global level and without mention of Na$^+_b$ specifically.

Recently, $^{23}$Na-MRI methods have been preferred clinically over spectroscopic methods. Such relaxometric modalities exploit differences in diffusion and relaxation behavior between Na$^+$ ions inside/outside the cell, because intracellular ions are generally considered less mobile due to binding. Due to the spin-3/2 of $^{23}$Na, this binding amplifies the relative contribution of nuclear satellite transitions and permits the use of MQF techniques to isolate signals from individual in vivo compartments. However, these $^{23}$Na-MRI methods are currently limited for probing intracellular Na$^+$ because they fail to completely suppress $^{23}$Na signals from the blood and interstitial compartments. While $^{23}$Na-MRI results with MQF or ADC can be compared with $^{23}$Na-MRSI results, duration of all experimental measurements will require several hours and may put strain on animal's physiology. However future studies can compare MRSI data with ADC and/or MQF data in different groups.

The method described herein avoids this practical $^{23}$Na-MRI limitation to provide physiological information about all relevant aqueous compartments, and thus enables estimation of transendothelial and transmembrane gradients. Overall, the $^{23}$Na-MRSI results agree with prior findings that a depolarized V$_m$ (i.e., weakened transmembrane gradient) is responsible for tumor proliferation. Given that both the cell membrane and BBB help to maintain the ionic level of the interstitial fluid, the results also show that the transendothelial gradient is significantly enhanced in the same tumors that show compromised BBB integrity (i.e., RG2 and U87). Together these suggest that the current $^{23}$Na-MRSI scheme can be used to study the perturbed sodium homeostasis in vivo within the neuropil.

This study is the first to image the transformed transmembrane and transendothelial gradients of gliomas using TmDOTP$^{5-}$ for 3D $^{23}$Na-MRSI at high spatial resolution (1 μL/voxel). The in vivo data consistently revealed weakening transmembrane gradient and strengthening transendothelial gradient within tumors compared to normal tissue, which partially agree with prior findings and suggest that tumors experience a redistribution of Na$^+$ across compartments. There is good evidence to propose that these measurements could potentially probe stages of the cell cycle (transmembrane gradient), and perhaps, angiogenic behavior (transendothelial gradient). The described $^{23}$Na-MRSI method could empower testing of novel chemotherapy and anti-angiogenic drugs for GBM models, which even at a preclinical level would be significant. This method can be translated into patients by using transition metal (II) ion-based or Gd$^{3+}$- based paraCA$^{n-}$ such that suitable therapies can be targeted based on MGMT screening in GBM patients.

In Vitro Characterization

In vitro experiments were performed using a 2-compartment coaxial cylindrical 7-inch NMR tube setup from WilmadLabGlass (Vineland, NJ, USA). One compartment contained 150 mM NaCl and the other contained the same but with varying amounts of TmDOTP$^{5-}$ (1-10 mM) and 10% v/v $^2$H$_2$O to lock the spectrometer frequency using the $^2$H$_2$O signal. NaCl and $^2$H$_2$O were purchased from Sigma-Aldrich (St. Louis, MO, USA), and TmDOTP$^{5-}$ was purchased as the sodium salt Na$_5$TmDOTP from Macrocyclics (Plano, TX, USA). The 5-mm opening of the NMR tube permitted an insert (the inner compartment) whose 50-mm-long tip had inner and outer diameters of 1.258 and 2.020 mm, respectively. The outer-to-inner volume ratio between the two compartments was 8.6. The geometry of the setup allowed 645 µL total in the outer compartment to fill around the tip. Each solution was pH-adjusted using HCl or KOH to give 5 different pH values.

$^{23}$Na-NMR spectra were collected on a Bruker Avance III HD 500 MHz vertical-bore spectrometer (Bruker, Billerica, MA, USA) interfaced with Bruker TopSpin v2.1 software. A Bruker 500 MHz TBO liquid broadband probe with z-gradient was used in all frequencies, and an inner coil was used to detect X-nuclei. A single $^{23}$Na square pulse (50 µs) was used to globally excite the volume of interest (repetition time T$_R$=275 ms) collecting 2048 free induction decay (FID) points in the time domain with an acquisition time t$_{aq}$=38.9 ms, averaged 4096 times. Each set of scans was repeated at a series of temperatures: 27, 30, 34, 37, and 40° C. Spectra were analyzed using 10 Hz line broadening (for improved delineation of major peaks and reduction of baseline noise) and manual zeroth- and first-order phasing. Data points were fit to Chebyshev rational polynomials using TableCurve 3D v4.0.05 (Systat Software, San Jose, CA, USA).

In Vivo Studies

The in vivo protocol was approved by the Institutional Animal Care & Use Committee of Yale University, and all procedures were performed in accordance with these enforced guidelines and regulations, and in compliance with the ARRIVE guidelines. Rats (athymic/nude and Fischer 344) were purchased through Yale University vendors. U251, U87 and RG2 GBM cell lines were purchased from American Type Culture Collections (Manassas, VA, USA). The U251, U87, and RG2 cells were cultured and grown in a 5% CO$_2$ incubator at 37° C. in either low-glucose (U251 cells) or high-glucose (U87 and RG2 cells) Dulbecco's Modified Eagle's Medium (DMEM) (Thermo Fisher Scientific, Waltham, MA, USA) with 10% fetal bovine serum (FBS) and 1% penicillin-streptomycin. Cells for tumor inoculation were harvested upon reaching at least 80% confluence and were prepared in FBS-free DMEM. Athymic/nude rats were injected intracranially with 2-5×10$^6$ tumor cells either from the U251 (n=6) or the U87 (n=8) cell line (5-µL aliquot) while placed in a stereotactic holder on a heating pad. Fischer 344 rats were injected with 1.25×10$^3$ RG2 cells (n=8). During the procedure, animals were anesthetized via isoflurane (Isothesia) inhalation (3-4%), purchased from Covetrus (Portland, ME, USA). Dissection was performed to the cranium, and a hole was drilled into the skull to allow for stereotactic needle insertion. Injections were performed using a 10-µL Hamilton syringe with a 26G needle into the right striatum for majority of the experiments, 3 mm to the right of the bregma and 3 mm below the dura. The cells were injected steadily at 1 µL/min over 5 min and the needle was left in place for an additional 5 min post-injection. The syringe was then gradually removed to preclude any backflow of cells. The hole in the skull was sealed with bone wax, and the incision site was sutured after removal of the syringe. Animals were given bupivacaine (2 mg/kg at incision site) and carprofen (5 mg/kg, subcutaneously) during the tumor inoculation to relieve pain. Carprofen was subsequently given once per day for two days post-inoculation.

Rats were weighed daily and kept on a standard diet of rat chow and water. Tumor growth was monitored every 3-4 days using $^1$H-MRI under isoflurane anesthesia. When the tumor had reached a minimum mean diameter of 3 mm at 20-24 days post-injection, each animal was imaged using $^1$H-MRI and $^{23}$Na-MRSI. An infusion line was first established through cannulation of the tail vein as a means to administer fluids and the paraCA$^{n-}$. During the cannulation procedure, the rat was placed on a heating pad to maintain physiological body temperature. A 30G needle, fitted onto a PE-10 line, was inserted into the tail vein while the animal was under anesthesia (also isoflurane 2-3%). The animal was then given Puralube Vet Ointment (Dechra, Overland Park, KS, USA) over the eyes and then situated in a prone position underneath an in-house built $^{23}$Na/$^1$H quad surface coil before being placed in the magnet. The 2.5-cm $^{23}$Na coil was placed directly on top of the head, and the two 5-cm $^1$H coils flanked the head on the left and right sides. Breathing rate was measured by placement of a respiration pad under the torso, and temperature was monitored through a rectal fiber-optic probe thermometer.

Imaging was conducted on a 9.4 T horizontal-bore Bruker Avance system (Billerica, MA), interfaced with Bruker ParaVision v6.0.1 software running on CentOS. Rats weighed 200-260 g at the time of imaging. Positioning and power optimizations for $^1$H signals were performed using Bruker-defined gradient-echo (GE) and fast spin-echo (FSE) sequences. Shimming was done on the $^1$H coils using an ellipsoid region (12×7×11 mm$^3$) to bring the water linewidth to less than 30 Hz using B$_0$ mapping with second-order shim corrections. Pre-contrast $^1$H anatomical MRI was first performed using a spin-echo sequence with 9 axial slices (FOV: 25×9×25 mm$^3$, 128×128 in-plane resolution) over 10 echo times T$_E$ (10-100 ms) with T$_R$=4 s). The multiple echo times enabled voxel-wise calculations of $^1$H T$_2$ values. $^{23}$Na power optimizations were then performed using a 2-ms 90° Shinnar-Le Roux (SLR) RF pulse over a 4096 Hz bandwidth (ν$_0$$^{Na}$=105.9 MHz at 9.4 T), where the optimal 90° pulse power was achieved using less than 8 W.

$^{23}$Na-MRSI in 3D was performed without slice selection using an SLR pulse, where the FOV was 25×19×25 mm$^3$ using a nominal voxel size of 1.0×1.0×1.0 mm$^3$ (i.e., point-spread function was ~2.24×2.24×2.24 mm$^3$), with T$_R$=300 ms, and phase encoding (gradient duration=1 ms, sweep width=8 kHz, encoding steps=1027, k-space radius factor=0.55) was done in all three spatial dimensions to avoid chemical shift artifacts caused by slice-selective RF pulses. A preliminary $^{23}$Na-MRSI scan (same parameters/conditions) was run before administering paraCA$^{n-}$. The in vivo $^1$H-MRI delineated the tumor and brain boundary and permitted co-registration with $^{23}$Na-MRSI data, both before and after infusion of paraCA$^{n-}$, enabling anatomical localization of $^{23}$Na-MRSI spectra at the voxel level. All spectra were line-broadened by 10 Hz and magnitude-corrected.

The animals were then given ~1 µL/g BW probenecid using a syringe pump (Harvard Apparatus, Holliston, MA, USA) for 10 min followed by a 20-min waiting period. Then Na$_5$TmDOTP (1 µmol/g BW) was co-infused with probenecid (same dose) at a rate of 15 µL/min. This infusion protocol with probenecid has been shown to increase TmDOTP$^{5-}$ retention in vivo without the need for renal ligation and yielded ~0.1 μmol TmDOTP$^{5-}$/g BW in the cortex and subcortex. Moreover, the slow infusion rate allows TmDOTP$^{5-}$ diffusion/clearance into other tissue during the infusion, and therefore TmDOTP$^{5-}$ does not accumulate and remain exclusively in the vasculature. Post-contrast $^{23}$Na-MRSI was performed 30 min after the start of infusion and repeated subsequently thereafter during the infusion. The imaging session was concluded with post-contrast $^{1}$H-MRI under identical conditions. Rats were sacrificed following imaging by isoflurane inhalation overdose (5%) while the animal was already unconscious during imaging.

Death was ensured by inducing bilateral pneumothorax. $^{1}$H-MRI and $^{23}$Na-MRSI results were processed and analyzed using home-written code in MATLAB (MathWorks, Natick, MA, USA). Voxel-wise $T_2$ values for $^{1}$H were calculated by fitting MRI voxel intensities versus the series of $T_E$ values to a monoexponential curve $e^{-TE/T2}$. Pre-contrast and post-contrast $^{1}$H $T_2$ values were used to qualitatively ascertain the success of paraCA$^{n-}$ infusion. 3D $^{23}$Na-MRSI data were reconstructed using Fourier transformation in all spatial and temporal dimensions after 10-Hz line-broadening. Individual $^{23}$Na peaks were identified and integrated in MATLAB, guided by the changes observed in $R_2$ maps from the $^{1}$H-MRI data which is roughly proportional to [TmDOTP$^{5-}$] within each voxel. Due to line broadening induced by TmDOTP$^{5-}$, the integration range was different for each compartment to capture the majority of each peak. Integration bandwidths were chosen based on in vitro results and amount of peak separation. The shift for each $^{23}$Na peak was based on the amount of TmDOTP$^{5-}$ present in each compartment, i.e., most shifted and broadest for blood compartment compared to the interstitial compartment, whereas the intracellular compartment was unshifted and narrowed. The $\Delta$Na$^{+}_{mem}$ values were calculated by subtracting ∫Na$^{+}_i$ from ∫Na$^{+}_e$, and $\Delta$Na$^{+}_{end}$ by subtracting ∫Na$^{+}_e$ from ∫Na$^{+}_b$.

$^{1}$H-DCE-MRI Studies

To measure vascular parameters [K$^{trans}$ (volume transfer coefficient, min$^{-1}$), F$_p$ (plasma flow rate, min$^{-1}$), v$_e$ (interstitial volume fraction, unitless), v$_p$ (plasma volume fraction, unitless)] from a two-compartment exchange model (2×CM), $^{1}$H-DCE-MRI was performed on a subset of RG2 (9.4 T), U87 (11.7 T) and U251 (11.7 T) tumors. $^{1}$H-DCE-MRI data used a $^{1}$H volume-transmit (8-cm)/surface-receive (3.5-cm) coil.

Baseline images for $T_1$ mapping were acquired using a rapid acquisition with relaxation enhancement (RARE) sequence with six $T_R$ values (0.4, 0.7, 1, 2, 4, 8 s). Seven 1-mm slices covering the extent of the tumor were chosen and images were acquired with a 25×25 mm FOV, 128×128 matrix and $T_E$ of 10 ms. $^{1}$H-DCE-MRI acquisition consisted of a dynamic dual-echo spoiled GE sequence with a temporal resolution of 5 s. Images were acquired with $T_R$=39.1 ms, $T_E$=2.5/5 ms, flip angle=15°, and one average. Three central slices of the tumor were chosen with identical positioning, FOV (25×25 mm), and matrix (128×128) to be co-registered to the $T_1$ data. The sequence was repeated every 5 s over a 22 min period with 0.25 μmol/g gadobutrol (Bayer, AG), a gadolinium (Gd$^{3+}$)-containing contrast agent, injected 2 min after the start of the sequence and then flushed with 100 μL heparinized saline. The multi-$T_R$ $T_1$ sequence was then repeated at the end of the $^{1}$H-DCE-MRI acquisition to serve as a post-Gd$^{3+}$ $T_1$ mapping which was used to delineate tumor boundaries. Quantitative $T_1$ maps were generated by fitting voxel-level data to a monoexponential function in MATLAB.

Measurements from $T_1$-weighted images before Gd$^{3+}$ injection were used to transform time-intensity curves into time-concentration curves after the bolus injection. The region of interest (ROI) was placed inside the tumor area, including the rim, as determined by the region of contrast enhancement/uptake. All analysis, including masking the ROI, was performed in MATLAB using the same home-written code. The arterial input function (AIF) was measured by collecting arterial blood samples at discrete time points post-injection. The raw AIF was fit to a bi-exponential curve with a linear upslope during injection of Gd$^{3+}$. Plasma [Gd$^{3+}$] was derived from the blood [Gd$^{3+}$] using a hematocrit of 0.45. The time resolution and duration interval used downstream in the analysis pipeline were adjusted manually.

The exchange-model parameters were estimated by fitting each voxel using Levenberg-Marquardt regression. Because K$^{trans}$ fitting often converged on local minima instead of the desired global minimum, multiple starting values were used, ultimately choosing the one with the smallest residual. Other variables were less sensitive to the initial condition, so a single starting value sufficed.

Subsequent Studies

Having established the utility of $^{23}$Na-MRSI in vivo with TmDOTP$^{5-}$, additional applications of Na$^+$ imaging were explored, such as monitoring therapeutic efficacy or using other agents to probe different spectroscopic characteristics. A separate cohort of U87 GBM models were treated with sorafenib, an anti-angiogenic tyrosine kinase inhibitor, with some animals kept as controls. Sorafenib treatment (0.1 g/kg body weight) began on day 9 following tumor inoculation and was dissolved in dimethylsulfoxide (DMSO) to be delivered via oral gavage. The sorafenib was able to slow tumor growth compared to untreated animals (FIG. 9), and that the Na$^+$ imbalances were contained within the tumor region for both untreated and treated animals. Therefore, $^{23}$Na-MRSI with TmDOTP$^{5-}$ has potential to effectively image the efficacy of cancer drugs.

Because the majority of the present studies looked at $^{23}$Na chemical shift, the line broadening capabilities of these paramagnetic agents were also interrogated. TmDOTP$^{5-}$ induced substantial $^{23}$Na line broadening within tumor models compared to normal tissue (FIGS. 10A-10F), and this can potentially be used as a biomarker for cancer. GdDOTP$^{5-}$, however, was found to have comparable broadening potential as TmDOTP$^{5-}$ but with smaller shiftability. This is due to the high magnetic moment of Gd$^{3+}$ which contributes to some degree of anisotropy to the paramagnetic susceptibility. Therefore, identical experiments were performed where GdDOTP$^{5-}$ was infused and found the $^{23}$Na line broadening to be larger within the tumor as well compared to healthy tissue. Moreover, the tumoral line broadening induced by GdDOTP$^{5-}$ correlated well with the increases in $\Delta$Na$^{+}_{end}$ and decreases in $\Delta$Na$^{+}_{mem}$ found by analysis of $^{23}$Na chemical shifts induced by TmDOTP$^{5-}$ (FIGS. 12A-12D). Crucially, this family of paramagnetic agents has allowed to insightful probing of the tumor microenvironment and drawing of significant conclusions about tumor aggressiveness based on spectroscopic analysis.

FIGS. 14A-14D illustrate concentration effects of Dotarem (gadorate meglumine or Gd$^{3+}$2-[4,7,10-tris(carboxymethyl)-1,4,7,10-tetrazacyclododec-1-yl]acetate) and Gadavist (gadobutrol or Gd$^{3+}$2,2',2''-(10-((2R,3S)-1,3,4-trihydroxybutan-2-yl)-1,4,7,10-tetraazacyclododecane-1,4,7-triyl)triacetate) on $^{23}$Na spectra. $^{23}$Na spectra are displayed for concentric tubes parallel to the magnetic field, where the agent added to the outer compartment in the phantom was (FIG. 14A) Dotarem, or (FIG. 14B) Gadavist. Spectra are shown for 20 mM, 10 mM, and 5 mM, where 0 ppm corresponds to the natural, unshifted $^{23}$Na resonance of the inner compartment to which no agent was added. The $^{23}$Na chemical shifts display a shiftability stronger than the other Gd$^{3+}$-based agents with macrocyclic chelates.

Statistics

All statistical comparisons were performed in MATLAB using a 2-sample Student's t-test (i.e., data passed normality tests with Prism in GraphPad, San Diego, CA) whose null hypothesis claimed there was no difference between the means of the two populations being tested. The populations in the present analysis were compartmental and gradient $^{23}$Na signal values (i.e., means and standard deviations of voxel-wise integrals) between tumor and normal tissue and between cohorts of different tumors. For $^1$H-DCE-MRI studies, the populations were different parameter values between different tumors. In all cases, a significance level of 0.05 was used.

ENUMERATED EMBODIMENTS

The following enumerated embodiments are provided, the numbering of which is not to be construed as designating levels of importance:

Embodiment 1 provides a method for detecting sodium ion irregularities in a patient, the method comprising at least one of the following: administering a volume of a metallic biosensor to a region of the patient; and detecting a volume of compartmentalized sodium ions within the region based on the administered volume of the metallic biosensor.

Embodiment 2 provides the method of embodiment 1, wherein the volume of compartmentalized sodium ions further comprises a volume of intracellular sodium ions, a volume of interstitial sodium ions, a volume of blood sodium ions, or a combination thereof.

Embodiment 3 provides the method of any one of embodiments 1-2, wherein the metallic biosensor comprises a polyanionic macrocyclic chelate complexing a lanthanide metal ion and/or a transition (II) metal ion.

Embodiment 4 provides the method of any one of embodiments 1-3, wherein the lanthanide (III) metal ion comprises at least one of La$^{3+}$, Ce$^{3+}$, Pr$^{3+}$, Nd$^{3+}$, Pm$^{3+}$, Sm$^{3+}$, Eu$^{3+}$, Gd$^{3+}$, Tb$^{3+}$, Dy$^{3+}$, Ho$^{3+}$, Er$^{3+}$, Tm$^{3+}$, Yb$^{3+}$, and Lu$^{3+}$.

Embodiment 5 provides the method of any one of embodiments 1-4, wherein the transition (II) metal ion comprises at least one of Mn$^{2+}$, Fe$^{2+}$, Co$^{2+}$, Ni$^{2+}$, and Cu$^{2+}$.

Embodiment 6 provides the method of any one of embodiments 1-5, wherein the polyanionic macrocyclic chelate comprises at least one of DOTA$^{4-}$ (2,2',2'',2'''-(1,4,7,10-Tetraazacyclododecane-1,4,7,10-tetrayl)tetraacetic acid), DOTP$^{8-}$ (1,4,7,10-Tetraazacyclododecane-1,4,7,10-tetra(methylene phosphonate), DOTMA$^{-4}$ ((1R,4R,7R,10R-α,α',α'',α'-tetramethyl-1,4,7,10 tetraazacyclododecane-1,4,7,10-tetraacetate), NOTP$^{-6}$ (1,4,7-Triazacyclononane-1,4,7-tri(methylene phosphonate), DOTA-4AmP$^{8-}$ (1,4,7,10-tetraazacyclododecane-1,4,7,10-tetrakis(acetamido-methylenephosphonate), and DO3A-butrol (2,2',2''-(10-((2R,3S)-1,3,4-trihydroxybutan-2-yl)-1,4,7,10-tetraazacyclododecane-1,4,7-triyl)triacetate).

Embodiment 7 provides the method of any one of embodiments 1-6, wherein the metallic biosensor comprises TmDOTP$^{-5}$, GdDOTP$^{5-}$, or a combination thereof.

Embodiment 8 provides the method of any one of embodiments 1-7, wherein the detecting further comprises: executing a magnetic resonance spectroscopic imaging (MRSI) process on the region of the patient.

Embodiment 9 provides the method of any one of embodiments 1-8, further comprising: identifying a tumor located in the region of the patient based on the volume of compartmentalized sodium ions.

Embodiment 10 provides the method of embodiment 9, wherein the tumor comprises a glioma tumor.

Embodiment 11 provides the method of any one of embodiments 1-10, further comprising: identifying a tumor type based on the volume of compartmentalized sodium ions.

Embodiment 12 provides the method of any one of embodiments 1-11, further comprising: detecting a volume of sodium ions in the region of the patient prior to the administering of the metallic biosensor; and comparing the volume of sodium ions to the volume of compartmentalized sodium ions.

Embodiment 13 provides the method of embodiment 12, wherein the comparing further comprises: identifying a difference in a number, an amplitude, a shift, or a combination thereof, between sodium ionic peaks contained in the volume of sodium ions and sodium ionic peaks contained in the volume of compartmentalized sodium ions.

Embodiment 14 provides the method of any one of embodiments 1-13, further comprising: detecting another volume of compartmentalized sodium ions within the region corresponding to a different location within the region; and comparing the volume of compartmentalized sodium ions to the other volume of compartmentalized sodium ions.

Embodiment 15 provides the method of embodiment 14, wherein the comparing further comprises: identifying a difference in a number, an amplitude, a shift, a line broadening or narrowing, or a combination thereof, between sodium ionic peaks contained in the volume of compartmentalized sodium ions and sodium ionic peaks contained in the other volume of compartmentalized sodium ions.

Embodiment 16 provides the method of any one of embodiments 1-15, further comprising: generating a transmembrane gradient mapping of the region of the patient according to the volume of compartmentalized sodium ions.

Embodiment 17 provides the method of any one of embodiments 1-16, further comprising at least one of the following: administering a treatment to the region subsequent to the detecting; administering another volume of a metallic biosensor to the region; and detecting another volume of compartmentalized sodium ions within the region based on the additionally administered volume of metallic biosensor.

Embodiment 18 provides the method of any one of embodiments 1-17, further comprising at least one of the following: comparing the volume of compartmentalized sodium ions and the other volume of compartmentalized sodium ions; and determining an efficacy of the administered treatment based on the comparison.

Embodiment 19 provides the method of any one of embodiments 1-18, wherein the volume of sodium ions is represented in a spectrum.

EQUIVALENTS

Although illustrative embodiments of the invention have been described using specific terms, such description is for illustrative purposes only, and it is to be understood that changes and variations may be made without departing from the spirit or scope of the following claims.

INCORPORATION BY REFERENCE

The entire contents of all patents, published patent applications, and other references cited herein are hereby expressly incorporated herein in their entireties by reference.

The invention claimed is:

1. A method for detecting sodium ion irregularities in a patient, the method comprising:
   administering a volume of a metallic biosensor to a region of the patient,
   wherein the metallic biosensor comprises a polyanionic macrocyclic chelate complexing a lanthanide (III) metal ion;
   detecting a volume of compartmentalized sodium ions within the patient's region based on the administered volume of the metallic biosensor using magnetic resonance spectroscopic imaging (MRSI);
   determining a three-dimensional spatial distribution of sodium ions within the patient's region,
   wherein the three-dimensional spatial distribution of sodium ions is at least one selected from the group consisting of intracellular sodium ions, interstitial sodium ions, and blood sodium ions; and
   generating a transmembrane gradient or transendothelial gradient mapping of the patient's region from the three-dimensional spatial distribution of the sodium ions.

2. The method of claim 1, wherein the lanthanide (III) metal ion comprises at least one of $La^{3+}$, $Ce^{3+}$, $Pr^{3+}$, $Nd^{3+}$, $Pm^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, and $Lu^{3+}$.

3. The method of claim 1, wherein the polyanionic macrocyclic chelate comprises $DOTP^{8-}$ (1,4,7,10-Tetraaza-cyclododecane-1,4,7,10-tetra(methylene phosphonate).

4. The method of claim 1, wherein the metallic biosensor comprises $TmDOTP^{5-}$, $GdDOTP^{5-}$, or a combination thereof.

5. The method of claim 1, further comprising:
   identifying a tumor located in the patient's region based on the volume of compartmentalized sodium ions.

6. The method of claim 5, wherein the tumor comprises a glioma tumor.

7. The method of claim 5, further comprising:
   identifying a tumor type based on the volume of compartmentalized sodium ions.

8. The method of claim 1, further comprising:
   detecting a volume of sodium ions in the patient's region prior to the administering of the metallic biosensor; and
   comparing the volume of sodium ions to the volume of compartmentalized sodium ions.

9. The method of claim 8, wherein the comparing further comprises:
   identifying a difference in a number, an amplitude, a shift, or a combination thereof, between sodium ionic peaks contained in the volume of sodium ions and sodium ionic peaks contained in the volume of compartmentalized sodium ions.

10. The method of claim 1, further comprising:
   detecting another volume of compartmentalized sodium ions within the patient's region corresponding to a different location within the patient's region; and
   comparing the volume of compartmentalized sodium ions to the other volume of compartmentalized sodium ions.

11. The method of claim 10, wherein the comparing further comprises:
   identifying a difference in a number, an amplitude, a shift, a line broadening or narrowing, or a combination thereof, between sodium ionic peaks contained in the volume of compartmentalized sodium ions and sodium ionic peaks contained in the other volume of compartmentalized sodium ions.

12. The method of claim 1, further comprising:
   administering a treatment to the patient's region subsequent to the detecting;
   administering an additional volume of metallic biosensors to the patient's region; and
   detecting another volume of compartmentalized sodium ions within the patient's region based on the additionally administered volume of metallic biosensor.

13. The method of claim 12, further comprising:
   comparing the volume of compartmentalized sodium ions and the other volume of compartmentalized sodium ions; and
   determining an efficacy of the administered treatment based on the comparison.

14. The method of claim 1, wherein the three-dimensional spatial distribution of sodium ions is represented in a spectrum.

15. The method of claim 1, wherein the three-dimensional spatial distribution has a spatial resolution of 1 μL/voxel.

* * * * *